US008383095B2

(12) United States Patent
Christensen et al.

(10) Patent No.: US 8,383,095 B2
(45) Date of Patent: Feb. 26, 2013

(54) METHODS AND COMPOSITIONS FOR ENHANCING ENGRAFTMENT OF HEMATOPOIETIC STEM CELLS

(75) Inventors: Julie Lynne Christensen, Boulder Creek, CA (US); Holger Karsunky, Redwood City, CA (US)

(73) Assignee: Cellerant Therapeutics, Inc., San Carlos, CA (US)

( * ) Notice: Subject to any disclaimer, the term of this patent is extended or adjusted under 35 U.S.C. 154(b) by 0 days.

(21) Appl. No.: 11/675,069

(22) Filed: Feb. 14, 2007

(65) Prior Publication Data
US 2007/0237752 A1    Oct. 11, 2007

Related U.S. Application Data

(60) Provisional application No. 60/773,405, filed on Feb. 14, 2006.

(51) Int. Cl.
*A01N 63/00* (2006.01)
*C12N 5/08* (2006.01)
*C12N 15/63* (2006.01)

(52) U.S. Cl. ................................. 424/93.1; 435/372

(58) Field of Classification Search .................. None
See application file for complete search history.

(56) References Cited

U.S. PATENT DOCUMENTS

| | | | |
|---|---|---|---|
| 5,137,809 A | | 8/1992 | Loken et al. |
| 5,199,942 A * | | 4/1993 | Gillis ........................ 604/4.01 |
| 5,750,397 A | | 5/1998 | Tsukamoto et al. |
| 5,840,580 A | | 11/1998 | Terstappen et al. |
| 5,877,299 A | | 3/1999 | Thomas et al. |
| 5,879,940 A | | 3/1999 | Torok-Storb et al. |
| 6,326,198 B1 | | 12/2001 | Emerson et al. |
| 6,335,195 B1 | | 1/2002 | Rodgers et al. |
| 6,338,942 B2 | | 1/2002 | Kraus et al. |
| 6,465,247 B1 * | | 10/2002 | Weissman et al. ............ 435/325 |
| 6,465,249 B2 | | 10/2002 | Reya et al. |
| 6,558,662 B2 * | | 5/2003 | Sykes et al. .................. 424/93.1 |
| 6,733,746 B2 | | 5/2004 | Daley et al. |
| 6,761,883 B2 | | 7/2004 | Weissman et al. |
| 6,967,029 B1 | | 11/2005 | Zsebo et al. |
| 7,618,654 B2 | | 11/2009 | Weissman et al. |
| 7,811,815 B2 * | | 10/2010 | Brown .......................... 435/325 |
| 2003/0060425 A1 | | 3/2003 | Ahlem et al. |
| 2004/0241856 A1 | | 12/2004 | Cooke |
| 2005/0118147 A1 | | 6/2005 | Oh |
| 2005/0215473 A1 | | 9/2005 | Alvarez et al. |
| 2006/0134783 A1 | | 6/2006 | Fong et al. |
| 2006/0222625 A1 * | | 10/2006 | Brown ........................ 424/85.1 |

FOREIGN PATENT DOCUMENTS

| | | |
|---|---|---|
| WO | WO 94/01534 A1 | 1/1994 |
| WO | WO 99/10478 A1 | 3/1999 |
| WO | WO 99/10748 A1 | 3/1999 |
| WO | WO 99/40180 A2 | 8/1999 |
| WO | WO 00/07002 A1 | 2/2000 |
| WO | WO 00/70022 A2 | 11/2000 |
| WO | WO 01/00019 A1 | 1/2001 |
| WO | WO 2004/024875 A2 | 3/2004 |
| WO | WO 2004/046312 A1 | 6/2004 |
| WO | WO 2004/046312 A2 | 6/2004 |
| WO | WO 2004/071443 A1 | 8/2004 |
| WO | WO 2004/071443 A2 | 8/2004 |

OTHER PUBLICATIONS

Bitmansour, Andrew et al.; "Myeloid progenitors protect against invasive aspergillosis and *Pseudomonas aeruginosa* infection following hematopoietic stem cell transplantation"; 2002, *Blood*, vol. 100, No. 13, pp. 4660-4667.

Christensen, Julie L. et al.; "Flk-2 is a marker in hematopoietic stem cell differentiation: A simple method to isolate long-term stem cells"; 2001, *PNAS*, vol. 98, No. 25, pp. 14541-14546.

Blair, Allison et al.; "Ex vivo expansion of megakaryocyte progenitor cells from normal bone marrow and peripheral blood and from patients with haematological malignancies"; 2002, *British Journal of Hematology*, vol. 116, pp. 912-119.

Drayer, A. Lyndsay et al.; "The in vitro effects of cytokines on expansion and migration of megakaryocyte progenitors"; 2000, *British Journal of Hematology*, vol. 109, pp. 776-784.

Domen et al.; "Neutropenic Mice Can Be Protected from Fungus Infection by Ex Vivo Expanded Allogenic Myeloid Progenitors"; *Blood* (ASH Annual Meeting Abstracts); vol. 106, Abstract No. 3038 (2005).

Akahori, H., et al., "Effects of pegylated recombinant human megakaryocyte growth and development factor on thrombocytopenia induced by a new myelosuppressive chemotherapy regimen in mice," *Stem Cells* 14(6):678-689 (Nov. 1996).

Akashi, et al., "Bcl-2 rescues T lymphopoiesis in interleukin-7 receptor-deficient mice," Cell, 89(7):1033-1041 (1997).

Akashi, et al., "Prospective Isolation of a Progenitor Common to all Myeloid Lineages and its Lineal Descendant Myelomonocytic and Erythroid/Megakaryocytic Progenitors," Blood, 94 (10, Suppl. 1 Part 1):377a (1999).

Akashi, K., "A clonogenic common myeloid progenitor that gives rise to all myeloid lineages," *Nature* 404(6774):193-197 (Mar. 2000).

Akashi, K., et al., "Lymphoid development from hematopoietic stem cells," *Int. J. Hematol.* 69(4):217-226 (Jun. 1999).

Akashi, K., et al., "Transcriptional accessibility for genes of multiple tissues and hematopoietic lineages is hierarchically controlled during early hematopoiesis," *Blood* 101(2):383-390 (Jan. 2003) (first pub'd online Sep. 5, 2002).

(Continued)

*Primary Examiner* — Quang Nguyen

(74) *Attorney, Agent, or Firm* — Kilpatrick Townsend & Stockton LLP

(57) ABSTRACT

The present disclosure relates to the field of hematopoietic stem cell transplantation. More specifically, methods, compositions and kits for improving engraftment of stem cell transplants by administering myeloid progenitor cells are provided.

13 Claims, 10 Drawing Sheets

OTHER PUBLICATIONS

Antoni, G., et al., "A short synthetic peptide fragment of human interleukin 1 with immunostimulatory but not inflammatory activity," *J. Immunol.* 137(10):3201-3204 (Nov. 1986).

Arber, C. et al., "MHC-mismatched murine committed myeloid progenitors engraft and protect against invasive aspergillosis", *Stanford University School of Medicine, Dept. of Medicine, Divisions of Bone Marrow Transplantation and Infectious Diseases*, Stanford CA 94305 USA, Abstract published in *Blood*, Nov. 16, 2003. Poster presented Dec. 8, 2003 at ASH.

Arber, et al., "Common lymphoid progenitors from MHC-mismatched donors engraft without inducing GVHD," *Blood*, 102:3504 (2003).

Barbone, F., et al., "New epoetin molecules and novel therapeutic approaches," *Nephrol. Dial Transplant.* 14(Supp. 2):80-84 (1999).

Barker, J., et al., "Impact of Multiple Unit Unrelated Donor Umbilical Cord Blood Transplantation in Adults: Preliminary Analysis of Safety and Efficacy," Abstract #2791, *Blood*, Grune & Stratton, New York, 98(11): 666a (2001).

Barry, S., et al., "Two contiguous residues in human interleukin-3, Asp21 and Glu22, selectively interact with the α- and β-chains of its receptor and participate in function," *J. Biol. Chem.* 269(11):8488-8492 (Mar. 1994).

Bartley, T., et al., "Identification and cloning of a megakaryocyte growth and development factor that is a ligand for the cytokine receptor Mpl," *Cell* 77(7):1117-1124 (Jul. 1994).

Beilhack, G., et al., "Prevention of Type I Diabetes with Major Histocompatibility Complex-Compatible and Nonmarrow Ablative Hematopoietic Stem Cell Transplants," Diabetes, vol. 54, pp. 1770-1779 (2005).

Bender, J. et al;, "Phenotypic analysis and characterization of CD34+ cells from normal human bone marrow, cord blood, peripheral blood and mobilized peripheral blood from patients undergoing autologous stem cell transplantation", *Clinical Immunology and Immunopathology*, vol. 70, No. 1, Jan. pp. 1-18, 1994.

Bertolini, F., et al., "Comparative study of different procedures for the collection and banking of umbilical cord blood," *J. Hematother.* 4(1):29-36 (Feb. 1995).

Bhatia, M., et al., "Quantitative analysis reveals expansion of human hematopoietic repopulating cells after short-term ex vivo culture," *J. Exp. Med.* 186(4):619-624 (Aug. 1997).

Bitmansour, et al. "Myeloid progenitors protect against invasive aspergillosis and *Pseudomonas aeruginosa* infection following hematopoietic stem cell transplantation", *Blood*, Dec. 15, 2002, vol. 100, No. 13.

Bittencourt, H., et al., "Association of CD34 cell dose with hematopoietic recovery, infections, and other outcomes after HLA-identical sibling bone marrow transplantation," *Blood*, vol. 99, No. 8, pp. 2726-2733 (2002).

Boissel, J., et al., "Erythropoietin structure-function relationships: Mutant proteins that test a model of tertiary structure," *J. Biol. Chem.* 268(21):15983-15993 (Jul. 1993).

Booth, et al., "Protection Against Mucosal Injury by Growth Factors and Cytokines," *J. Natl. Cancer Inst. Monogr.*, 29:16-20 (2001).

Boraschi, D., et al., "Structure-function relationship in the IL-1 family," *Front. Biosci.* 1:270-308 (Oct. 1996).

Broudy, V., "Stem cell factor and hematopoiesis," *Blood* 90(4):1345-1364 (Aug. 1997).

Broxmeyer, H., et al., "High-efficiency recovery of functional hematopoietic progenitor and stem cells from human cord blood cryopreserved for 15 years," *Proc. Natl. Acad. Sci. USA* 100(2):645-650 (Jan. 2003) (first pub'd online Jan. 7, 2003).

Burger, H., "Cloning and expression of interleukin-3 genes of chimpanzee and new world monkeys," *Biochim. Biophys. Acta* 1217(2):195-198 (Mar. 1994).

Cairo, MS, et al., "Circulating granulocyte colony-stimulating facotr (G-CSF) levels after allogeneic and autologous bone marrown transplantation: endogenous G-CSF production correlates with myeloid engraftment," *Blood*, 79:1869-1873 (1992).

Chardon, P., et al., "The porcine major histocompatibility complex and related paralogous regions: a review," *Genet. Sel. Evol.* 32(2):109-128 (Mar.-Apr. 2000).

Chiu, C., et al., "Multiple biological activities are expressed by a mouse interleukin 6 cDNA clone isolated from bone marrow stromal cells," *Proc. Natl. Acad. Sci. USA* 85(19):7099-7103 (Oct. 1988).

Christensen, J., et al., "Flk-2 is a marker in hematopoietic stem cell differentiation: a simple method to isolate long-term stem cells," *Proc. Natl. Acad. Sci. USA* 98(25):14561-14568 (Dec. 2001) (first pub'd online Nov. 27, 2001).

Cohen, D., et al., "Cloning and expression of the rat interleukin-3 gene," *Nucleic Acids Res.* 14(9):3641-3658 (May 1986).

Coutinho, L., et al., "Clonal and long term bone marrow cultures using human bone marrow," in *Haemotology: A Practical Approach*, N. Testa, et al. (eds.), Oxford University Press: Oxford, GB (1992), pp. 75-106.

Curtis, B., et al., "Enhanced hematopoietic activity of a human granulocyte/macrophage colony-stimulating factor-interleukin 3 fusion protein," *Proc. Natl. Acad. Sci. USA* 88(13):5809-5813 (Jul. 1991).

Dagan, S., et al., "High-level expression and production of recombinant human interleukin-6 analogs," *Protein Expr. Purif.* 3(4):290-294 (Aug. 1992).

Dasgupta, A., et al., "Methods of stem cell mobilization," *J. Infusional Chemother.* 6(1):12-16 (Winter 1996).

David, R., et al., "The porcine erythropoietin gene: cDNA sequence, genomic sequence and expression analyses in piglets," *Domest. Anim. Endocrinol.* 20(2):137-147 (Feb. 2001).

Devine, S., et al., "Clinical application of hematopoietic progenitor cell expansion: current status and future prospects," *Bone Marrow Transplant.* 31(4):241-252 (Feb. 2003).

Dexter, T., et al., "Conditions controlling the proliferation of haemopoietic stem cells in vitro," *J. Cell Physiol.* 91(3):335-344 (Jun. 1977).

Droogmans, L., et al., "Nucleotide sequence of bovine interleukin-6 cDNA," *DNA Seq.* 2(6):411-413 (1992).

Dunham, S., et al., "Isolation, nucleotide sequence and expression of a cDNA encoding feline granulocyte colony-stimulating factor," *Cytokine* 14(6):347-351 (Jun. 2001).

Ebrahimi, B., et al., "Cloning, sequencing and expression of the ovine interleukin 6 gene," *Cytokine* 7(3):232-236 (Apr. 1995).

Enver, et al., "Do Stem Cells Play Dice?" *Blood*, 92(2):348-351 (1998).

Feese, M., et al., "Structure of the receptor-binding domain of human thrombopoietin determined by complexation with a neutralizing antibody fragment," *Proc. Natl. Acad. Sci. USA* 101(7):1816-1821 (Feb. 2004) (first publ'd online Feb. 9, 2004).

Fernandez, M., et al., "Unrelated umbilical cord blood transplants in adults: Early recovery of neutrophils by supportive co-transplantation of a low number of highly purified peripheral blood CD34+ cells from an HLA-haploidentical donor," Experimental Hematology 31, pp. 535-544 (2003).

Fisher, J., "Erythropoietin: physiologic and pharmacologic aspects," *Proc. Soc. Exp. Biol. Med.* 216(3):358-369 (Dec. 1997).

Foster, D., et al., "Human thrombopoietin: gene structure, cDNA sequence, expression, and chromosomal localization," *Proc. Natl. Acad. Sci. USA* 91(26):13023-13027 (Dec. 1994).

Fox, N., et al., "Thrombopoietin expands hematopoietic stem cells after transplantation," *J. Clin. Invest.* 110(3):387-394 (Aug. 2002).

Fu, P., et al., "The sheep erythropoietin gene: molecular cloning and effect of hemorrhage on plasma erythropoietin and renal/liver messenger RNA in adult sheep," *Mol. Cell Endocrinol.* 93(2):107-116 (Jun. 1993).

Fugier-Vivier, I., et al., "Plasmacytoid precursor dendritic cells facilitate allogenic hematopoietic stem cell engraftment," *J. Experimental Medicine*, vol. 201, No. 3, pp. 373-383 (2005).

Fung, M.-C., et al., "Molecular cloning of cDNA for murine interleukin-3," *Nature* 307(5948):233-237 (Jan. 1984).

Galy, A., et al., "Human T, B, natural killer, and dendritic cells arise from a common bone marrow progenitor cell subset," *Immunity* 3(4):459-473 (Oct. 1995).

Gasson, J., et al., "Molecular characterization and expression of the gene encoding human erythroid-potentiating activity," *Nature* 315(6022):768-771 (Jun. 1985).

Georgopoulos, et al., "The Role of the Ikaros Gene in Lymphocyte Development and Homeostasis," *Annu. Rev. Immunol.*, 15:155-176 (1997).

Gill, T., et al., "Current status of the major histocompatibility complex in the rat," *Transplant. Proc.* 27(2):1495-1500 (Apr. 1995).

Gluckman, et al., "Factors associated with outcomes of unrelated cord blood transplant: Guidelines for donor choice," *Exp. Hematol.*, 32:397-407 (2004).

Greiner, D., et al., "SCID mouse models of human stem cell engraftment," *Stem Cells* 16(3):166-177 (1998).

Grewal, S., et al., "Unrelated donor hematopoietic cell transplantation: marrow or umbilical cord blood?" *Blood*, 101:11; pp. 4233-4244 (2003).

Gronenborn, A., et al., "A 1H-NMR study of human interleukin-1 beta. Sequence-specific assignment of aromatic residues using site-directed mutant proteins," *Eur. J. Biochem.* 161(1):37-43 (Nov. 1986).

Gryn, J., et al., "Multiple Unmatched Umbilical Cord Units (MUCs) for Adult Allogeneic Transplantation," Abstract #2792, *Blood*, Grune & Stratton, New York, 98(11): 666a (2001).

Gurney, A., et al., "Genomic structure, chromosomal localization, and conserved alternative splice forms of thrombopoietin," *Blood* 85(4):981-988 (Feb. 1995).

Han, S., et al., "Cloning and expression of the cDNA encoding rat granulocyte colony-stimulating factor," *Gene* 175(1-2):101-104 (Oct. 1996).

Harman, B., et al., "Mouse plasmacytoid dendritic cells derive exclusively from estrogen-resistant myeloid progenitors," *Blood*, vol. 108, No. 3, pp. 878-885 (2006).

Heidari, M., et al., "Cloning, sequencing, and analysis of cDNA encoding bovine granulocyte-colony stimulating factor," *Vet. Immunol. Immunopathol.* 73(2):183-191 (Feb. 2000).

Heimfeld, et al., "The in vitro Response of Phenotypically Defined Mouse Stem Cells and Myeloerythroid Progenitors to Single or Multiple Growth Factors," Proc. Natl. Acad. Sci. USA, 88:9902-9906 (1991).

Heise, E., et al., "The major histocompatibility complex of primates," *Genetica* 73(1-2):53-68 (Aug. 1987).

Henschler, R., et al., "Maintenance of transplantation potential in ex vivo expanded CD34(+)-selected human peripheral blood progenitor cells," *Blood* 84(9):2898-2903 (Nov. 1994).

Hill, C., et al., "The structure of granulocyte-colony-stimulating factor and its relationship to other growth factors," *Proc. Natl. Acad. Sci. USA* 90(11):5167-5171 (Jun. 1993).

Hirano, T., et al., "Complementary DNA for a novel human interleukin (BSF-2) that induces B lymphocytes to produce immunoglobulin," *Nature* 324(6092):73-76 (Nov. 1986).

Howard, R., et al., "Cloning of equine interleukin 1 alpha and equine interleukin 1 beta and determination of their full-length cDNA sequences," *Am. J. Vet. Res.* 59(6):704-711 (Jun. 1998).

Huang, J., et al., "Muteins of human interleukin-1 that show enhanced bioactivities," *FEBS Lett.* 223(2):294-298 (Nov. 1987).

Huether, M., et al., "Cloning, sequencing and regulation of an mRNA encoding porcine interleukin-1 β," *Gene* 129(2):285-289 (Jul. 1993).

Iwasaki-Arai, J., et al., "Enforced granulocyte/macrophage colony-stimulating factor signals do not support lymphopoiesis, but instruct lymphoid to myelomonocytic lineage conversion," *J. Exp. Med.* 197(10)1311-1322 (May 2003).

Jagerschmidt, A., et al., "Human thrombopoietin structure-function relationships: identification of functionally important residues," *Biochem. J.* 333(Pt. 3):729-734 (Aug. 1998).

Jones, M. et al. "Refolding and Oxidation of Recombinant Human Stem Cell Factor Produced in *Escherichia coli*", *J. Bio. Chem.* vol. 271, No. 19, pp. 11301-11308, (1998).

Kanamaru, S., et al., "Low Numbers of Megakaryocyte Progenitors in Grafts of Cord Blood Cells May Result in Delayed Platelet Recovery After Cord Blood Cell Transplant," Stem Cells, vol. 18, No. 3, pp. 190-195 (2000).

Kato, K., et al., "Isolation and characterization of CD34+ hematopoietic stem cells from human peripheral blood by high-gradient magnetic cell sorting," *Cytometry* 14(4):384-392 (1993).

Kennedy, M., et al., "A common precursor for primitive erythropoiesis and definitive haematopoiesis," *Nature* 386(6624):488-493 (Apr. 1997).

Ketterer, G.S. et al., "High CD34+Cell Counts Decrease Hematologic Toxicity of Autologus Peripheral Blood Progenitor Cell Transplantation", *Blood*, vol. 91, No. 9 pp. 3148-3155, (1998).

Kiel, M., "SLAM Family Receptors Distinguish Hematopoietic Stem and Progenitor Cells and Reveal Endothelial Niches for Stem Cells," *Cell*, 121(7):1109-21 (2005).

Kessinger, A., et al., "Erythropoietin for mobilizations of circulating progenitor cells in patients with previously treated relapsed malignancies," *Exp. Hematol.* 23:609-612 (1995).

Kondo, M., et al., "Identification of clonogenic common lymphoid progenitors in mouse bone marrow," *Cell* 91(5):661-672 (Nov. 1997).

Kydd, J., et al., "Report of the First International Workshop on Equine Leucocyte Antigens, Cambridge, UK, Jul. 1991," *Vet. Immunol. Immunopathol.* 42(1):3-60 (Jul. 1994).

Langley, K., et al., "Properties of variant forms of human stem cell factor recombinantly expressed in *Escherichia coli*," *Arch. Biochem. Biophys.* 311(1):55-61 (May 1994).

Langley, K., et al., "Purification and characterization of soluble forms of human and rat stem cell factor recombinantly expressed by *Escherichia coli* and by Chinese hamster ovary cells," *Arch. Biochem. Biophys.* 295(1):21-28 (May 1992).

Lapidot, T., et al., "Current understanding of stem cell mobilization: the roles of chemokines, proteolytic enzymes, adhesion molecules, cytokines, and stromal cells," *Exp. Hematol.* 30(9):973-981 (Sep. 2002).

Laughlin, M.J., et al., "Outcomes after Transplantation of Cord Blood or Bone Marrow from Unrelated Donors in Adults with Leukemia," *N. Eng. J. Med.*, 351:22, pp. 2265-2275 (2004).

Lee, S., et al., "Outcomes Research in Hematopoietic Cell Transplantation," pp. 434-446, 2007. In Thomas's Hematopoietic Cell Transplantation, 3rd Edition.

Leong, S., et al., "The nucleotide sequence for the cDNA of bovine interleukin-1 β," *Nucleic Acids Res.* 16(18):9054 (Sep. 1988).

Lev, S., et al., "Interspecies molecular chimeras of kit help define the binding site of the stem cell factor," *Mol. Cell Biol.* 13(4):2224-2234 (Apr. 1993).

Lewin, H., et al., "Comparative organization and function of the major histocompatibility complex of domesticated cattle," *Immunol. Rev.* 167:146-158 (Feb. 1999).

Lin, F., et al., "Monkey erythropoietin gene: cloning, expression and comparison with the human erythropoietin gene," *Gene* 44(2-3):201-209 (1986).

Lin, Y., et al., "Serial granulocyte transfusions as a treatment for sepsis due to multidrug-resistant *Pseudomonas aeruginosa* in a neutropenic patient," *J. Clin. Microbiol.* 41(10):4892-4893 (Oct. 2003).

Lin., F., et al., "Cloning and expression of the human erythropoietin gene," *Proc. Natl. Acad. Sci. USA* 82(22):7580-7584 (Nov. 1985).

Lok, S., et al., "Cloning and expression of murine thrombopoietin cDNA and stimulation of platelet production in vivo," *Nature* 369(6481):565-568 (Jun. 1994).

Lok, S., et al., "The structure, biology and potential therapeutic applications of recombinant thrombopoietin," *Stem Cells* 12(6):586-598 (Nov. 1994).

Lopez, A., et al., "A human interleukin 3 analog with increased biological and binding activities," *Proc. Natl. Acad. Sci. USA* 89(24):11842-11846 (Dec. 1992).

Lovejoy, B., et al., "Crystal structure of canine and bovine granulocyte-colony stimulating factor (G-CSF)," *J. Mol. Biol.* 234(3):640-653 (Dec. 1993).

Lu, H., et al., "Isolation and characterization of a disulfide-linked human stem cell factor dimer. Biochemical, biophysical, and biological comparison to the noncovalently held dimmer," *J. Biol. Chem.* 271(19):11301-11316 (May 1996).

Lu, L., et al., "Influence in vitro of IL-3/Epo fusion proteins compared with the combination of IL-3 plus Epo in enhancing the proliferation of single isolated erythroid and multipotential progenitor cells from human umbilical cord blood and adult bone marrow," *Exp. Hematol.* 23(10):1130-1134 (Sep. 1995).

Lyman, S., et al., "Biology and potential clinical applications of flt3 ligand," *Curr. Opin. Hematol.* 2(3):177-181 (May 1995).

Lyman, S., et al., "Cloning of the human homologue of the murine flt3 ligand: a growth factor for early hematopoietic progenitor cells," *Blood* 83(10):2795-2801 (May 1994).

Lyman, S., et al., "Molecular cloning of mast cell growth factor, a hematopoietin that is active in both membrane bound and soluble forms," *Cell* 75(6):1157-1167 (Dec. 1993).

Magli, et al., "Transient Nature of Early Hematopoietic Spleen Colonies," Nature, 295:527-529 (1982).

Magro, E., et al., "Early hematopoietic recovery after single unit unrelated cord blood transplantation in adults supported by co-infusion of mobilized stem cells from a third party donor," haematologica/the hematology journal; 91(5) (2006, pp. 640-648.

Manz, et al., "Prospective isolation of human clonogenic common myeloid progenitors," *Proc. Natl. Acad. Sci. USA* 99(18):11872-11877 (Sep. 2002) (first pub'd online Aug. 22, 2002).

March, C., et al., "Cloning, sequence and expression of two distinct human interleukin-1 complementary DNAs," *Nature* 315(6021):641-647 (Jun. 1985).

Martin, F., et al., "Primary structure and functional expression of rat and human stem cell factor DNAs," *Cell* 63(1):203-211 (Oct. 1990).

Mavroudis, D., et al., "CD34+ cell dose predicts survival, post-transplant morbidity, and rate of hematologic recovery after allogeneic marrow transplants for hematologic malignancies," Blood, vol. 88, No. 8, pp. 3223-3229 (1996).

McCullough, J., et al., "Effects of storage of granulocytes on their fate in vivo," *Transfusion* 23(1):20 (Jan.-Feb. 1983).

McInnes, C., et al., "Cloning of a cDNA encoding bovine interleukin-3," *Gene* 139(2):286-290 (Feb. 1994).

McInnes, C.J. et al., "The Cloning and Expression of the cDNA for Ovine Stem Cell Factor(Kit-Ligand) and Charecterization of its Vitro Haematopoietic Activity", *Cytokine*, vol. 11, No. 4 (Apr. 1999) pp. 249-256.

McNeice, I. et al., "Ex vivo expanded peripherap blood progenitor cells provide rapid neutrophil recovery after high dose chemotherapy in patients with breast cancer," *Blood*, vol. 96 No. 9 (Nov. 2000), pp. 3001-3007.

Metcalf, "Lineage Commitment and Maturation in Hematopoietic Cells: The Case for Extrinsic Regulation," Blood, 92(2):345-352 (1998).

Mickelson, E., et al., *Hematopoietic Cell Transplantation*, E. Thomas (ed.), pp. 28-37, Blackwell Scientific Press: Malden, MA (1999).

Middleton, D., et al., *Methods in Molecular Biology: MHC Protocols* 210:67-112 (2002).

Miyadai, K., et al., "Importance of the carboxy-terminus of human interleukin-11 in conserving its biological activity," *Biosci. Biotechnol. Biochem.* 60(3):541-542 (Mar. 1996).

Miyamoto, et al., "Persistence of Multipotent Progenitors Expressing AMLI/ETO Transcripts in Long-Term Remission Patients with t(8;21) Acute Myelogenous Leukemia," Blood, 87(11):4789-4796 (1996).

Miyamoto, T., et al., "Myeloid or lymphoid promiscuity as a critical step in hematopoietic lineage commitment," *Dev. Cell* 3(1):137-147 (Jul. 2002).

Montillo, M., et al., "Successful CD34+ cell mobilization by intermediate-dose Ara-C in chronic lymphocytic leukemia patients treated with sequential fludarabine and Campath-1H," *Leukemia* 18(1):57-62 (Jan. 2004).

Morishima, Y., et al., "The clinical significance of human leukocyte antigen (HLA) allele compatibility in patients receiving a marrow transplant from serologically HLA-A, HLA-B, and HLA-DR matched unrelated donors," *Blood* 99(11):4200-4206 (Jun. 2002).

Morris, C., et al., "Mobilization of CD34+ cells in elderly patients ($\geq$70 years) with multiple myeloma: influence of age, prior therapy, platelet count and mobilization regimen," *British J. Hematol.* 120:413-423 (2003).

Morrison, et al., "The Aging of Hematopoietic Stem Cells," Nature Medicine, 2(9):1011-1016 (1996).

Morrison, et al., "The Long-Term Repopulating Subset of Hematopoietic Stem Cells is Deterministic and Isolatable by Phenotype," Immunity, 1:661-673 (1994).

Mullighan, C., et al., "Genomic Polymorphism and Allogeneic Hematopoietic Transplantation Outcome," *American Society for Blood and Marrow Transplantation, Biology of Blood and Marrow Transplantation*, 12:19-27 (2006).

Mwangi, S., et al., "Cloning of the bovine interleukin-3-encoding cDNA," *Gene* 162(2):309-312 (Sep. 1995).

O'Brien, S., et al., "Comparative genome organization of the major histocompatibility complex: lessons from the *Felidae*," *Immunol. Rev.* 167:133-144 (Feb. 1999).

O'Doherty, U. et al., "Dendritic Cells Freshly Isolated from Human Blood Express CD4 and Mature into Typical Immunstimulatory Dendrtic cells after Culture in Monocyteconditioned Medium," J. Exp. Med. Uni. Press, vol. 178, 1993 1067-1078.

Ogami, K., et al., "The sequence of a rat cDNA encoding thrombopoietin," *Gene* 158(2):309-310 (Jun. 1995).

Ogawa, "Differentiation and Proliferation of Hematopoietic Stem Cells," Blood, 81(11):2844-2853 (1993).

Ohsumi, J., et al., "Adipogenesis inhibitory factor. A novel inhibitory regulator of adipose conversion in bone marrow," *FEBS Lett.* 288(1-2):13-16 (Aug. 1991).

Okubo, T., et al., "Stroma-dependent maintenance of cytokine responsive hematopoietic progenitor cells derived from long-term bone marrow culture," *Cell Struct. Funct.* 25(2):133-139 (Apr. 2000).

Olins, P., et al., "Saturation mutagenesis of human interleukin-3," *J. Biol. Chem.* 270(40):23754-23760 (Oct. 1995).

Olivieri, A., et al., "Factors affecting hemopoietic recovery after high-dose therapy and autologous peripheral blood progenitor cell transplantatioini: a single center experience," *Haematologica*, 83:329-337 (1998).

Orita, T., et al., "Polypeptide and carbohydrate structure of recombinant human interleukin-6 produced in Chinese hamster ovary cells," *J. Biochem.* (Tokyo) 115(2):345-350 (Feb. 1994).

Orkin, "Development of the Hematopoietic System," Current Biology, 6:597-602 (1996).

Ormerod, M.G., Flow Cytometry: A Practical Approach, 3rd Ed., Oxford University Press (2000), pp. vii-xi.

Otsuka, T., et al., "Isolation and characterization of an expressible cDNA encoding human IL-3. Induction of IL-3 mRNA in human T cell clones," *J. Immunol.* 140(7):2288-2295 (Apr. 1988).

Palaszynski, E., "Synthetic C-terminal peptide of IL-1 functions as a binding domain as well as an antagonist for the IL-1 receptor," *Biochem. Biophys. Res. Commun.* 147(1):204-211 (Aug. 1987).

Park, H., et al., "Identification of functionally important residues of human thrombopoietin," *J. Biol. Chem.* 273(1):256-261 (Jan. 1998).

Passegue, E., et al., "Normal and leukemic hematopoiesis: Are leukemias a stem cell disorder or a reacquisition of stem cell charactersistics?" PNAS, vol. 100, Supp. 1, pp. 11842-11849 (2003).

Paul, S., et al., "Molecular cloning of a cDNA encoding interleukin 11, a stromal cell-derived lymphopoietic and hematopoietic cytokine," *Proc. Natl. Acad. Sci. USA* 87(19):7512-7516 (Oct. 1990).

Perkins, H., et al., "The complete cDNA sequences of IL-2, IL-4, IL-6 and IL-10 from the European rabbit (*Oryctolagus cuniculus*)," *Cytokine* 12(6):555-565 (Jun. 2000).

Petersdorf, E., et al., "Optimizing outcome after unrelated marrow transplantation by comprehensive matching of HLA class I and II alleles in the donor and recipient," *Blood* 92(10):3515-2520 (Nov. 1998).

Pevny, et al., "Erythroid Differentiation in Chimaeric Mice Blocked by a Target Mutation in the Gene for Transcription Factor GATA-1," Nature, 349:257-260 (1991).

Pflumio, F., et al., "Phenotype and function of human hematopoietic cells engrafting immune-deficient CB17-severe combined immunodeficiency mice and nonobese diabetic-severe combined immunodeficiency mice after transplantation of human cord blood mononuclear cells," *Blood* 88(10):3731 (Nov. 1996).

Piacibello, W., et al., "Engraftment in nonobese diabetic severe combined immunodeficient mice of human CD34(+) cord blood cells after ex vivo expansion: evidence for the amplification and self-renewal of repopulating stem cells," *Blood* 93(11):3736-3749 (Jun. 1999).

Ploemacher, R., et al., "An in vitro limiting-dilution assay of long-term repopulating hematopoietic stem cells in the mouse," *Blood* 74(8):2755-2763 (Dec. 1989).

Priestle, J., et al., "Crystallographic refinement of interleukin 1β at 2.0 A resolution," *Proc. Natl. Acad. Sci. USA* 86(24):9667-9671 (Dec. 1989).

Regidor, C., et al., "Cord Blood Transplantation Supported by Co-Infusion of CD133-Positive Hematopoietic Stem Cells from a Third Party Donor: Preliminary Results," Abstract #290, Biology of Blood and Marrow Transplantation, vol. 12, No. 2, Supp. 1 (Feb. 2006).

Reichle, A., et al., "Autologous tandem transplantation: almost complete reduction of neutropenic fever following the second transplantation by ex vivo expanded autologous myeloid postprogenitor cells," *Bone Marrow Transplant.* 32(3):299-305 (Aug. 2003).

Reiffers, J., et al., "Abrogation of post-myeloablative chemotherapy neutropenia by ex-vivo expanded autologous CD34-positive cells," *Lancet* 354(9184):1092-1093 (Sep. 1999).

Richel, D. J. et al., "Highly purified CD34+cells isolated using magnetic activated cell selection provide rapid engraftment following high dose chemotherapy in breast cancer patients", *Bone Marrow Transplantation* (2000) 25, 243-249.

Rocha, V., et al., "Transplants of Umbilical-Cord Blood or Bone Marrow from Unrelated Donors in Adults with Leukemia," *N. Eng. J. Med.*, 351:22, pp. 2276-2285 (2004).

Rosnet, O. et al., "Murine Flt 3, a gene encoding a novel tyrosine kinase receptor of the PDGFR/CSFIR family," *Oncogene* (1991), 6, 1641-1650.

Rosnet, O., et al., "Close physical linkage of the FLT1 and FLT3 genes on chromosome 13 in man and chromosome 5 in mouse," *Oncogene* (1993) 8:173-179.

Savvides, S., et al., "Flt3 ligand structure and unexpected commonalities of helical bundles and cystine knots," *Nat. Struct. Biol.* 7(6):486-491 (Jun. 2000).

Scheinkonig, C., et al., "Adoption of long-term cultures to evaluate the cryoprotective potential of trehalose for freezing hematopoietic stem cells," *Bone Marrow Transplant.* 34(6):531-536 (Sep. 2004).

Schwarz F. S., et al., TNF in combination with GM-CSF enhances the differentiation of neonatal cord blood stem cells into dendritic cells and macrophages, *Journal of Leukocyte Biology*, vol. 52, 1992, pp. 274-281.

Shamblott, et al., "Derivation of pluripotent stem cells from cultured human primordial germ cells," *Proc. Natl. Acad. Sci. USA* 95:13726-13731 (1998).

Shanafelt, A.B. et al., "Identification of critical regions in mouse granulocyte-macrophage colony-stimulating factor by scanning-ddetection analysis," *Proc. Natl. Acad. Sci.* USA vol. 86, pp. 4872-4876, 1989.

Shapiro, F., et al., "The effects of Flk-2/flt3 ligand as compared with c-kit ligand on short-term and long-term proliferation of CD34+ hematopoietic progenitors elicited from human fetal liver, umbilical cord blood, bone marrow, and mobilized peripheral blood," *J. Hematother.* 5(6):655-662 (Dec. 1996).

Shapiro, H., *Practical Flow Cytometry*, 4th ed., Wiley-Liss (2003). [General Guidance on Fluorescence Activated Cell Sorting], pp. vii-xxvi.

Shin, I. et al., "Cloning of canine GM-CSF and SCF genes", *J. Vet. Sci.*, 2(3), 159-166 (2001).

Shinkai, Y., et al., "RAG-2-deficient mice lack mature lymphocytes owing to inability to initiate V(D)J rearrangement," *Cell* 68(5):855-867 (Mar. 1992).

Shivdasani, et al., "A Lineage-Selective Knockout Establishes the Critical Role of Transportation Factor GATA-1 in Megakaryocyte Growth and Platelet Development," The EMBO Journal, 16(13):3965-3973 (1997).

Shizuru, J., "The Experimental Basis for Hematopoietic Cell Transplantation for Autoimmune Diseases," pp. 324-343, (2007). In Thomas's Hematopoietic Cell Transplatation.

Shoemaker, C., et al., "Murine erythropoietin gene: cloning, expression, and human gene homology.," *Mol. Cell Biol.* 6(3):849-858 (Mar. 1986).

Siminovitch, et al., "The Distribution of Colony-Forming Cells Among Spleen Colonies," Journal of Cellular and Comparative Physiology, 62(3):327-336 (1963).

Singh, "Gene Targeting Reveals a Hierarchy of Transcription Factors Regulating Specification of Lymphoid Cell Fates," Current Biology, 8:160-165 (1996).

Singhal, S., et al., "A low CD34+ cell dose results in higher mortality and poorer survival after blood or marrow stem cell transplantation from HLA-identical siblings: should $2\times10^6$ CD34+ cells/kg be considered the minimum threshold?" *Bone Marrow Transplantation*, 26, 489-96 (2000).

Sitnicka, et al., "The Effect of Thrombopoietin on the Proliferation and Differentiation of Murin Hematopoietic Stem Cells," Blood, W.B. Saunders, Philadelphia, PA, vol. 87, No. 12, pp. 4998-5005 (1996).

Skelly, S., et al., "High-level expression of a biologically active human interleukin-6 mutein," *J. Biotechnol.* 34(1):79-86 (Apr. 1994).

Souyri, M., et al., "A putative truncated cytokine receptor gene transduced by the myeloproliferative leukemia virus immortalizes hematopoietic progenitors," *Cell* 63(6):1137-1147 (Dec. 1990).

Spangrude, G., et al., "Purification and characterization of mouse hematopoietic stem cells," *Science* 241(4861):58-62 (Jul. 1988).

Steinam, RM., "Linking innate to adaptive immunity through dendritic cells," Novartis Found Symp., 279:101-9 (2006).

Storms, R., et al., "Isolation of primitive human hematopoietic progenitors on the basis of aldehyde dehydrogenase activity," *Proc. Natl. Acad. Sci. USA* 96(16):9118-9123 (Aug. 1999).

Stoyan, T., et al., "Recombinant soluble human interleukin-6 receptor. Expression in *Escherichia coli*, renaturation and purification," *Eur. J. Biochem.* 216(1):239-245 (Aug. 1993).

Suda, et al., "Analysis of Differentiation of Mouse Hematopoietic Stem Cells in Culture by Sequential Replating of Paired Proienitors," Blood, 64(2):393-399 (1984).

Sudo, Y., et al., "Synergistic effect of FLT-3 ligand on the granulocyte colony-stimulating factor-induced mobilization of hematopoietic stem cells and progenitor cells into blood in mice," *Blood* 89(9):3186-3191 (May 1997).

Suliman, H., et al., "Cloning of a cDNA encoding bovine erythropoietin and analysis of its transcription in selected tissues," *Gene* 171(2):275-280 (Jun. 1996).

Sutherland, H., et al., "Functional characterization of individual human hematopoietic stem cells cultured at limiting dilution on supportive marrow stromal layers," *Proc. Natl. Acad. Sci. USA* 87(9):3584-3588 (May 1990).

Swiderski, C., et al., "Molecular cloning, sequencing, and expression of equine interleukin-6," *Vet. Immunol. Immunopathol.* 77(3-4):213-220 (Dec. 2000).

Szilvassy, S. et al., "Quantitation of Murine and Human Hematopoietic Stem Cells by limiting-dilution analysis in competitively repopulated hosts,"*Meth in Mod Med*. vol. 63, Hematopoietic Stem Cell Protocols, C.A. Klug and C.T. Jordan, eds.; Humana Press Inc., Totowas, N.J., pp. 167-187, 2002.

Tacken, I., et al., "Definition of receptor binding sites on human interleukin-11 by molecular modeling-guided mutagenesis," *Eur. J. Biochem.* 265(2):645-655 (Oct. 1999).

Telford, J., et al., "The murine interleukin 1 β gene: structure and evolution," *Nucleic Acids Res.* 14(24):9955-9963 (Dec. 1986).

Terskikh, A., et al.; "Gene expression analysis of purified hematopoietic stem cells and committed progenitors," *Blood* 102(1):94-101 (Jul. 2003) (first pub'd online Mar. 6, 2003).

Thomson, J., et al., "Embryonic Stem Cell Lines Derived from Human Blastocysts," *Science*, 282:1145 (1998).

Traver, D., et al., "Fetal liver myelopoiesis occurs through distinct, prospectively isolatable progenitor subsets," *Blood* 98(3):627-635 (Aug. 2001).

Traver, et al., "Mice Defective in Two Apoptosis Pathways in the Myeloid Lineage Develop Acute Myeloblastic Leukemia," *Immunity*, 9:47-57 (1998).

Tsuchiya, M., et al., "Isolation and characterization of the cDNA for murine granulocyte colony-stimulating factor," *Proc. Natl. Acad. Sci. USA* 83(20):7633-7637 (Oct. 1986).

Turner, C., et al., "A modified harvest technique for cord blood hematopoietic stem cells," *Bone Marrow Transplant.* 10(1):89-91 (Jul. 1992).

Uchida, et al., "Rapid and Sustained Hematopoietic Recovery in Lethally Irradiated Mice Transplaned with Purified $Thy-1.1^{lo}$ $Lin^{-}-Sca-1^{+}$ Hematopoietic Stem Cells," *Blood*, 83(12):3758-3779 (1994).

Uchida, N., et al., "High doses of purified stem cells cause early hematopoietic recovery in syngeneic and allogeneic hosts," *J. Clin. Invest.* 101(5):961-966 (Mar. 1998).

Vaughn, R., "HLA Typing by Restriction Fragment Length Polymorphism Analysis," *Methods in Molecular Biology: MHC Protocols* 210:45-60 (2002).

Vilalta, A., et al., "Rabbit EPO gene and cDNA: expression of rabbit EPO after intramuscular injection of pDNA.," *Biochem. Biophys. Res. Commun.* 284(3):823-827 (Jun. 2001).

Wada, T., et al., "Characterization of the truncated thrombopoietin variants," *Biochem. Biophys. Res. Commun.* 213(3):1091-1098 (Aug. 1995).

Wagemaker, G., et al., "Interleukin-3," *Biotherapy* 2(4):337-345 (1990).

Wagner, et al., "Transplantation of unrelated donor umbilical cord blood in 102 patients with malignant and nonmalignant diseases: influence of CD34 cell does and HLA disparity on treatment-related mortality and survival," *Blood*, 100:51, pp. 1611-1618 (2002).

Wagner, J., et al., "Organization of the canine major histocompatibility complex: current perspectives," *J. Hered.* 90(1):35-38 (Jan.-Feb. 1999).

Wardley, et al., "Prospective evaluation of oral mucositis in patients receiving myeloablative conditioning regimens and haemopoietic progenitor rescue," *British Journal of Haematology*, 110:292-299 (2000).

Wen, D., et al., "Erythropoietin structure-function relationships: high degree of sequence homology among mammals," *Blood* 82(5):1507-1516 (Sep. 1993).

Wright, D., et al., "Cyclophosphamide/granulocyte colony-stimulating factor causes selective mobilization of bone marrow hematopoietic stem cells into the blood after M phase of the cell cycle," *Blood* 97(8):2278-2285 (Apr. 2001).

Yang, S. et al., "Molecular cloning of canine and feline FLT3 ligand reveals high degree of similarity to the human and mouse homologue but uniquely long cytoplasmic domain," *DNA Sequence*, 2000, vol. 11 (1-2) pp. 163-1166.

Yang, Y.-C., et al., "Human IL-3 (multi-CSF): identification by expression cloning of a novel hematopoietic growth factor related to murine IL-3," *Cell* 47(1):3-10 (Oct. 1986).

Yin, A., et al., "AC133, a novel marker for human hematopoietic stem and progenitor cells," *Blood* 90(12):5002-5012 (Dec. 1997).

Young, P., et al., "Cloning of rabbit interleukin-1 beta: differential evolution of IL-1 α and IL-1 β proteins," *Protein Eng.* 2(7):545-551 (May 1989).

Zhang, J., et al., "Purification and characterization of a recombinant murine interleukin-6. Isolation of N- and C-terminally truncated forms," *Eur. J. Biochem.* 207(3):903-913 (Aug. 1992).

Zhang, Z., et al., "Crystal structure of human stem cell factor: implication for stem cell factor receptor dimerization and activation," *Proc. Natl. Acad. Sci. USA* 97(14):7732-7737 (Jul. 2000).

Zhao, C., et al., "Overexpression and characterization of recombinant human fusion protein IL-6/IL-2 (CH925)," *Stem Cells* 12(3):339-347 (May 1994).

Zimmerman, T., et al., "Clinical impact of ex vivo differentiated myeloid precursors after high-dose chemotherapy and peripheral blood progenitor cell rescue," *Bone Marrow Transplant.* 26(5):505-510 (Sep. 2000).

Zon, et al., "Activiation of the Erythropoietin Receptor Promoter by Transcription Factor GATA-1," *Proc. Natl. Acad. Sci. USA*, 88:10638-10641 (1991).

\* cited by examiner

| Transplant Model | Cell Dose | | % Survival | Long Term Chimerism |
|---|---|---|---|---|
| Syngeneic | 50 KTLS | n = 14 | 57 % | ≤ 94 % |
| | 50 KTLS + 100K MP | n = 15 | 87 % | ≤ 92 % |
| Allogeneic | 100 KTLS | n = 15 | 26 % | ≤ 68 % |
| | 100 KTLS + 200K MP | n = 10 | 60 % | ≤ 93 % |
| Matched Unrelated | 250 KTLS | n = 10 | 60 % | ≤ 80 % |
| | 250 KTLS + 200K MP | n = 5 | 100% | ≤ 81 % |
| | 500 KTLS | n = 5 | 0 % | N/A |
| | 500 KTLS + 200K MP | n = 10 | 40 % | ≤ 89 % |
| Allogeneic C57/B6-> Balb/c | 1000 KTLS | n = 5 | 0 % | N/A |
| | 1000 KTLS + 200K MP | n = 5 | 20 % | ≤ 0.13 % |
| | 2000 KTLS | n = 5 | 40 % | ≤ 95 % |
| | 2000 KTLS + 200K MP | n = 5 | 60 % | ≤ 93 % |

FIG. 6

METHODS AND COMPOSITIONS FOR ENHANCING ENGRAFTMENT OF HEMATOPOIETIC STEM CELLS

1. CROSS-REFERENCE TO RELATED APPLICATIONS

This application claims the benefit under 35 U.S.C. §119(e) of U.S. Ser. No. 60/773,405 filed Feb. 14, 2006, which is hereby incorporated by reference in its entirety.

2. FIELD

The present teachings relate to methods and compositions for improved stem cell therapy, and in particular, to methods and compositions for facilitating the engraftment of suboptimal doses of hematopoietic stem cells.

3. INTRODUCTION

Hematopoietic stem cell transplantation (HSCT) is a critical component of the treatment of a wide array of hematologic disorders. Generally, there are two types of HSCTs: autologous and allogeneic transplantation. Autologous transplantation involves infusion of a recipient's own cells following myeloablative treatment. Autologous cell transplants minimize the risk of graft versus host disease (GVHD) and result in reduced complications. Allogeneic transplantation involves infusion of donor stem cells, typically using a donor that matches the recipient's MHC. However, matched unrelated donor (MUD) transplants are also associated with a stronger graft versus host reaction, and thus result in higher mortality rates.

There are three main sources of hematopoietic stem cells (HSC): bone marrow, peripheral blood, and umbilical cord blood. Umbilical cord blood (UCB) is a practical alternative source to other hematopoietic progenitor sources (e.g., bone marrow and mobilized peripheral blood) for related and unrelated allogeneic hematopoietic stem cell transplantation. Unfortunately, however, although cord blood is readily available and shows lower incidences of graft versus host disease, it is characterized by delayed engraftment.

Accordingly, while there is enormous promise for treating hematologic disorders with HSC obtained from cord blood, the slow rate of hematopoietic recovery remains a major obstacle. Laughlin, et al., *N. Eng. J. Med.* 351:22; 2265-2275 (2004). Cryopreserved nucleated cell (NC) dose is a major determinant of neutrophil recovery, and higher $CD34^+$ cell dose is associated with improved survival in unrelated donor UCB transplantation. Laughlin et al. Adult recipients of UCB with infused cell dose of less than $1.8 \times 10^7$ NC/kg or less than $1.7 \times 10^5$ $CD34^+$ cells/kg recipients body typically have inferior engraftment and survival. Wagner et. al., *Blood.* 100; 51 1611-1618. Particularly poor results have been seen with UCB when the nucleated cell dose is lower than $1.5 \times 10^7$ kg. Grewal, et al. *Blood,* 101; 1; 4233-4244.

There is also a well-established relationship between the level of human leukocyte antigen (HLA) mismatch and survival in HSCT. For example, there is a higher probability of survival in receipts of UCB grafts that are disparate in no more than two HLAs when the graft contains at least $1.7 \times 10^5$ $CD34^+$ cells/kg. Wagner et al.

Consequently, a consensus is emerging that UCB grafts with higher cell dose are needed for optimal engraftment in adult patients. Rocha et al. suggest that a unit of cord blood should have at least $2.0 \times 10^7$ nucleated cell/kg at the time of freezing and no more than two disparities in the matching for HLA, B or DRB1, alone or in combination with the recipient. Rocha et al., *N. Eng. J. Med.* 351:22; 2276-2285 (2004). While the minimum acceptable infused UCB graft cell dose is yet to be agreed upon, a minimum acceptable dose of about $1.5 \times 10^7$ nucleated cells/kg to about $1.7 \times 10^5$ kg $CD34^+$ cells has been suggested. Grewal et al., Wagner et. al.

In any event, even with UCG cell doses at or above these amounts, the efficiency of engraftment is still significantly less than with HSC from bone marrow or peripheral blood. Rocha et al, p. 2281 and FIG. 1A. Moreover, engraftment has been shown to worsen with the presence of even a single mismatch. Gluckman et al, *Exp. Hematol.* 32:397-407 (2004). Accordingly, there is still great interest in enhancing the engraftment of HSC obtained from UCB so as to improve the efficacy of stem cell transplantation.

4. SUMMARY

In accordance with the present disclosure, methods, compositions and kits for improving stem cell transplants are described. Specifically, methods for facilitating the engraftment of hematopoietic stem cells (HSC) are provided, comprising administering a myeloid progenitor cell (MP) graft to a transplant patient in conjunction with an HSC graft. The MP graft may be autologous or allogeneic to the HSC graft and/or to the patient, and may further comprise a mixed population of allogeneic MP cells. In a preferred embodiment, the MP cells are expanded in vitro prior to administration.

As demonstrated herein, the administration of MP in conjunction with HSC can dramatically enhance engraftment of the HSC, particularly in subjects receiving a suboptimal dose of HSC. Accordingly, in one aspect, methods for enhancing the engraftment of a suboptimal HSC graft are provided, comprising administering an MP graft to the patient in conjunction with the HSC graft. Generally, optimal HSC dosing is a function of the number of nucleated cells (NC) and/or $CD34^+$ cells in the HSC graft, and/or the level of mismatch at the MHC between the patient and HSC graft.

In one aspect, an optimal HSC graft requires a threshold number of cells/kg patient in order to achieve a successful stem cell transplantation. An optimal HSC graft will generally contain at least about $1.0 \times 10^6$ CD34+ cells per kg/patient, at least about $2.0 \times 10^6$ CD34+ cells per kg/patient, preferably at least about $3.0 \times 10^6$ CD34+ cells per kg/patient, more preferably at least about $4.0 \times 10^6$ CD34+ cells per kg/patient, and most preferably greater than $5.0 \times 10^6$ CD34+ cells per kg/patient.

Accordingly, in one aspect, the methods of the present invention employ MP grafts in conjunction with suboptimal HSC grafts, which will generally comprise less than about $5.0 \times 10^6$ CD34+ cells per kg/patient, more specifically less than about $4.0 \times 10^6$ CD34+ cells per kg/patient, preferably less than about $3.0 \times 10^6$ CD34+ cells per kg/patient, more preferably less than about $2.0 \times 10^6$ CD34+ cells per kg/patient, or most preferably less than about $1.0 \times 10^6$ CD34+ cells per kg/patient.

In some embodiments, the suboptimal graft is obtained from bone marrow or peripheral blood. In one embodiment, the suboptimal graft comprises less than about $5 \times 10^8$ nucleated cells/kg patient for infusion, more preferably less than 4.5 or $4.0 \times 10^8$ nucleated cells/kg patient, and most preferably less than about $4.1 \times 10^8$ nucleated cells/kg patient. In an alternative embodiment, the suboptimal graft may comprise less than about $6 \times 10^6$ $CD34^+$ cells/kg patient for infusion, more preferably less than about 4.5 to $5.5 \times 10^6$ $CD34^+$ cells/kg patient/kg, and most preferably less than about $5.0 \times 10^6$ $CD34^+$ cells/kg of patient.

In some embodiments, the suboptimal graft is obtained from umbilical cord blood. In one embodiment, the suboptimal graft comprises HSC derived from fewer than two cord blood units, and more preferably, from a single cord blood unit. In another embodiment, the suboptimal graft comprises less than about $4\times10^7$ nucleated cells/kg patient for infusion, more preferably less than $3.0\times10^7$ nucleated cells/kg patient, and most preferably less than about $3.5\times10^7$ nucleated cells/kg patient. In an alternative embodiment, the suboptimal graft may comprise less than about $5\times10^5$ CD34$^+$ cells/kg patient, more preferably less than about 3.5 to $4.5\times10^5$ CD34$^+$ cells/kg patient/kg, and most preferably less than about $4.0\times10^5$ CD34$^+$ cells/kg patient.

In another aspect, the suboptimal graft comprises HSC having more than one MHC mismatch in comparison with the patient phenotype.

Also provided are compositions for improving stem cell transplantation. In one aspect, the compositions comprise an autologous or allogeneic mixture of hematopoietic stem cells and myeloid progenitor cells. In one embodiment, the MP cells are expanded prior to combination with the HSC. Kits are also provided for isolating, expanding, preserving and administering MP and HSC in accordance with the subject methods.

5. FIGURES

The skilled artisan will understand that the figures are for illustration purposes only, and are not intended to limit the scope of the present teachings in any way.

FIG. 6 summarizes the survival and chimerism data for the three transplant models (syngeneic, matched unrelated donor, and mismatched allogeneic).

Figure 7B:
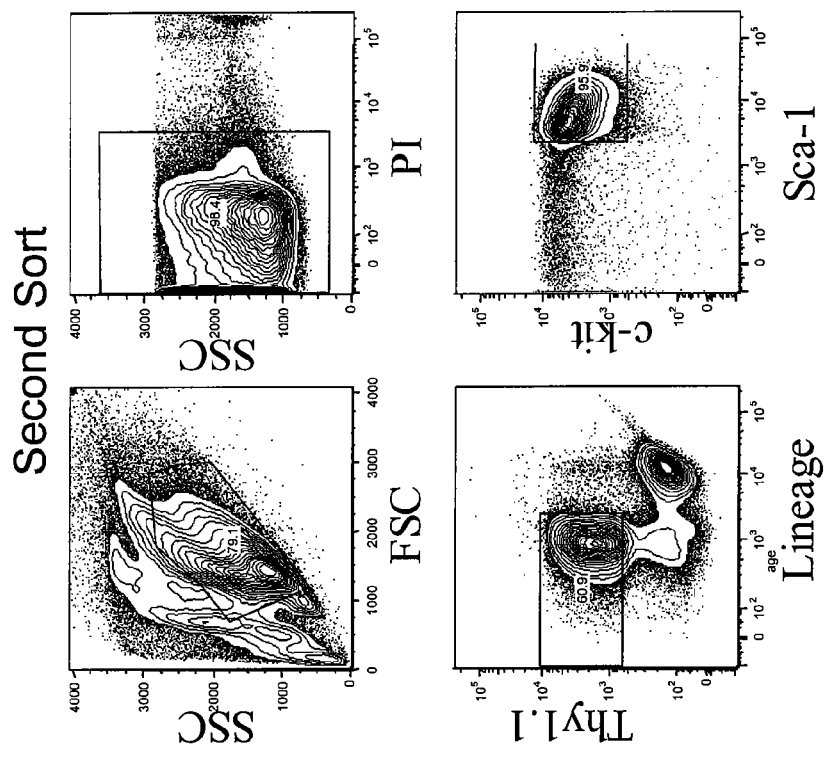
Figure 7A:
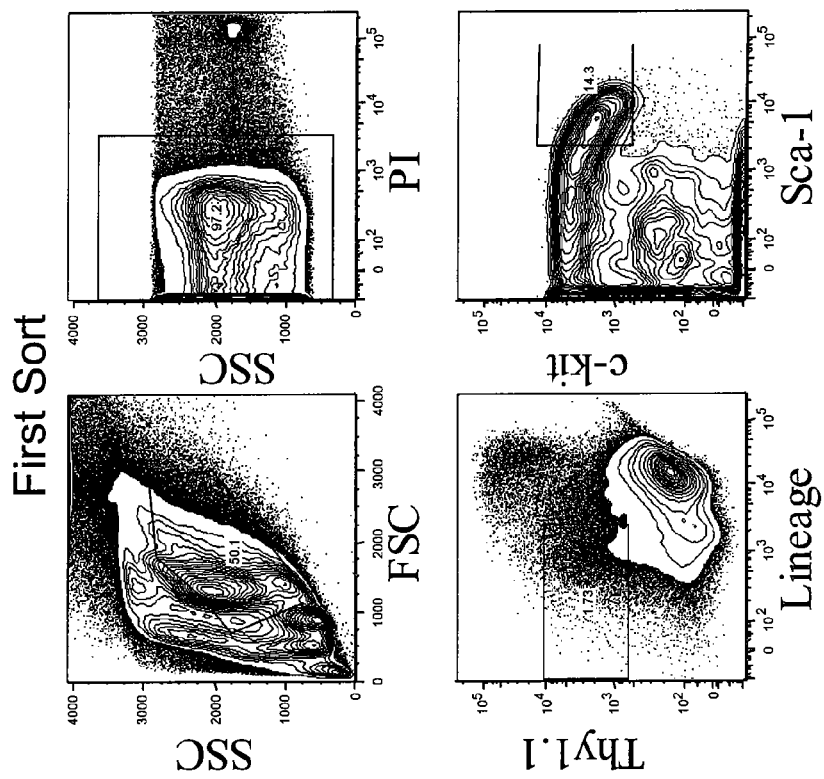

FIG. 7 shows sorting used to purify KTLS C57B6/Ka (Thy-1.1, CD45.1, H2b) HSC used in example 3.

Figures 8A, 8B:
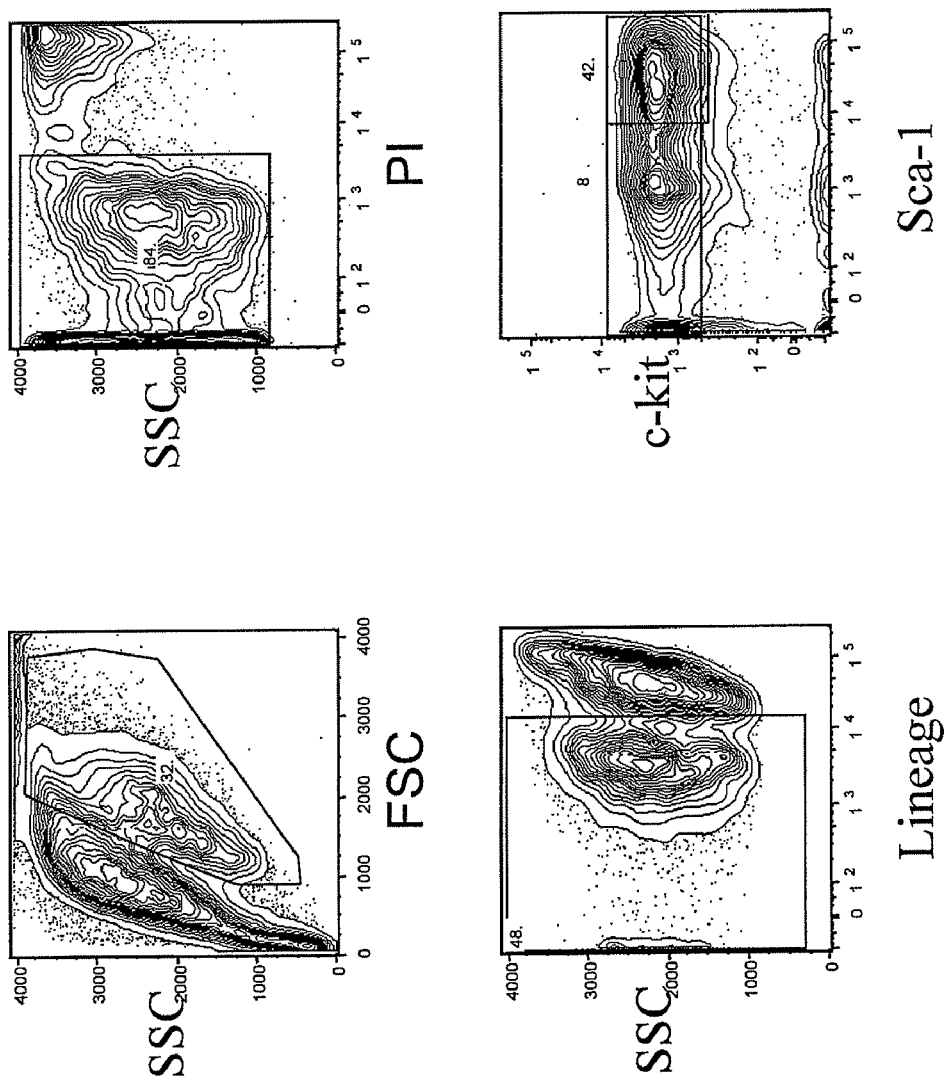

FIG. 8 shows the analysis of AKR (Thy-1.1, CD45.2, H2k) cultured derived MP.

Figure 9:
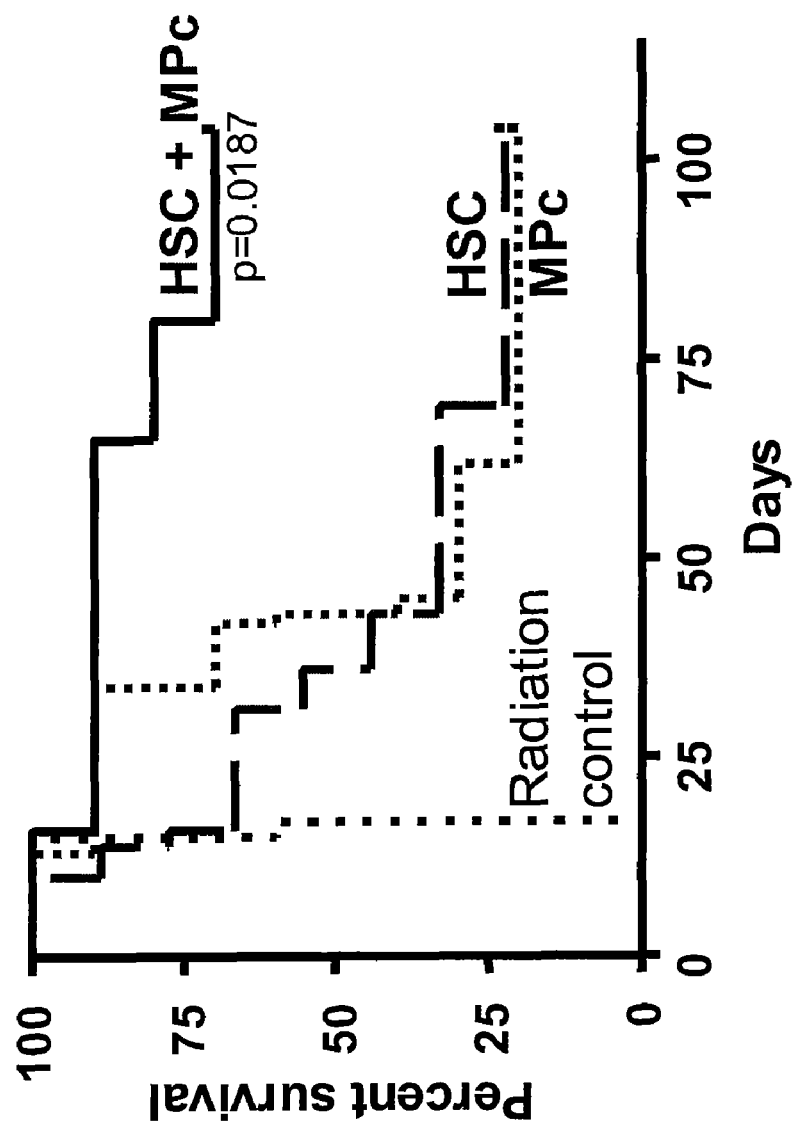

FIG. 9 shows survival data in transplantation model in which matched unrelated donor KTLS HSC were co-transplanted with completely mismatched allogeneic culture derived MP.

Figure 10:
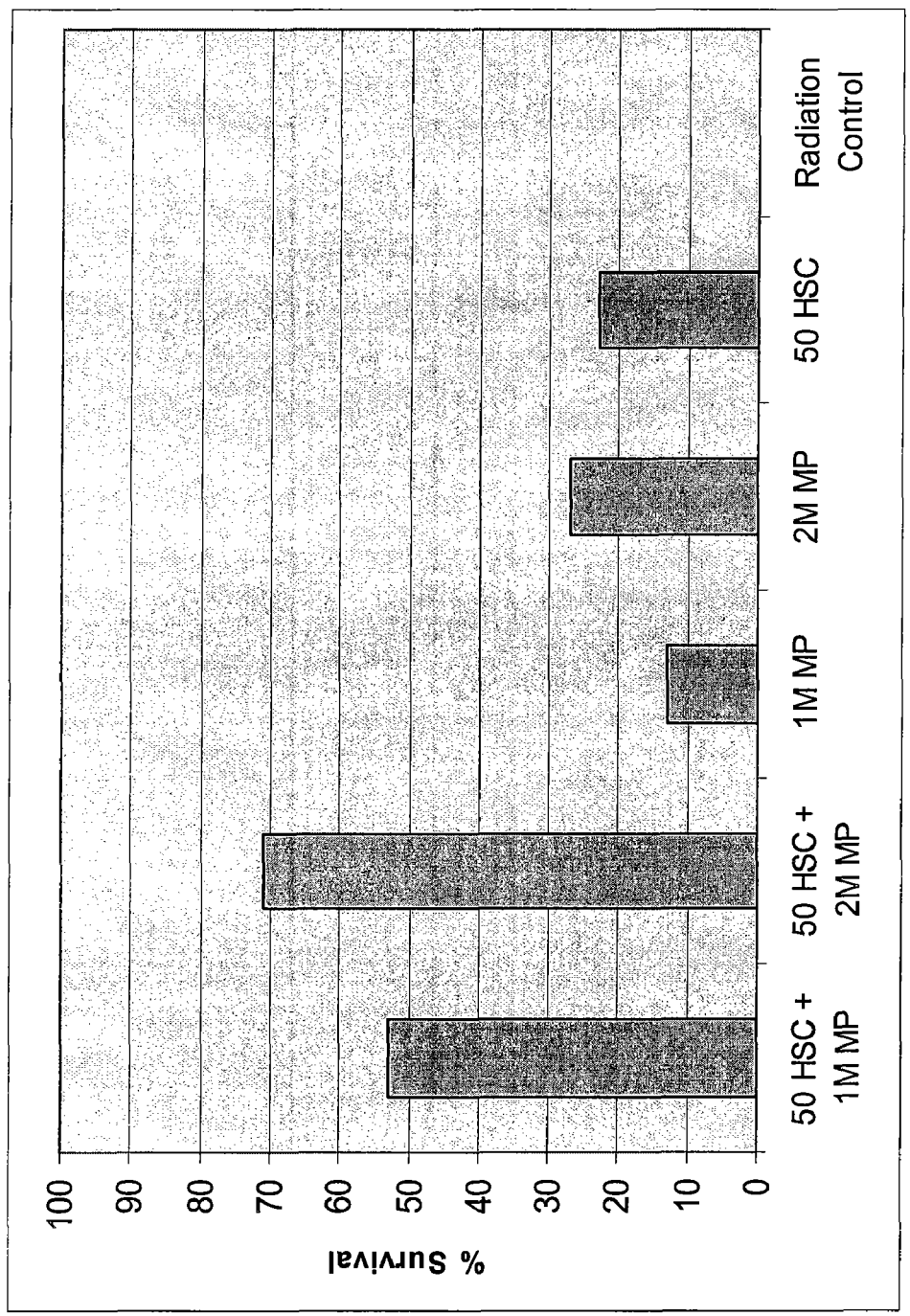

FIG. 10 shows survival data in a transplantation model in which MHC matched unrelated donor HSC were co-transplanted with MPc derived from 2 MHC mismatched donors.

6. DETAILED DESCRIPTION

6.1 Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor.

"Autologous" refers to deriving from or originating in the same subject or patient. An "autologous transplant" refers to collection and retransplant of a subject's own cells or organs.

"Committed myeloid progenitor cell" or "myeloid progenitor cell" or "MP" refers to a multipotent or unipotent progenitor cell capable of ultimately developing into any of the terminally differentiated cells of the myeloid lineage, but which do not typically differentiate into cells of the lymphoid lineage. Hence, "myeloid progenitor cell" refers to any progenitor cell in the myeloid lineage. Committed progenitor cells of the myeloid lineage include oligopotent CMP, GMP, and MEP as defined herein, but also encompass unipotent erythroid progenitor, megakaryocyte progenitor, granulocyte progenitor, and macrophage progenitor cells. Different cell populations of myeloid progenitor cells are distinguishable from other cells by their differentiation potential, and the presence of a characteristic set of cell markers.

"Common myeloid progenitor cell" or "CMP" refers to a cell characterized by its capacity to give rise to granulocyte/monocyte (GMP) progenitor cells and megakaryocyte/erythroid (MEP) progenitor cells. These progenitor cells have limited or no self-renewing capacity, but are capable of giving rise to myeloid dendritic, myeloid erythroid, erythroid, megakaryocytes, granulocyte/macrophage, granulocyte, and macrophage cells.

"Congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus.

"Expansion" or "expanded" in the context of cells refers to increase in the number of a characteristic cell type, or cell types, from an initial population of cells, which may or may not be identical. The initial cells used for expansion need not be the same as the cells generated from expansion. For instance, the expanded cells may be produced by ex vivo or in vitro growth and differentiation of the initial population of cells. Excluded from this term are limiting dilution assays used to characterize the differentiation potential of cells.

"Functional" in the context of cells refers to cells capable of performing or cells that retain the regular functions or activity associated with the specified cell type, as identified by a defined functional assay or assays. For instance, a "functional GMP cell" is a progenitor cell capable of ultimately differentiating into granulocytes and macrophages, where the terminally differentiated cells function as normal granulocytes and macrophages.

"Graft-versus-host response" or "GVH" or "GVHD" refers to a cellular response that occurs when lymphocytes of a different MHC class are introduced into a host, resulting in the reaction of the lymphocytes against the host.

"Granulocyte/macrophage progenitor cell" or "GMP" refers to a cell derived from common myeloid progenitor cells, and characterized by its capacity to give rise to granulocyte and macrophage cells, but which does not typically give rise to erythroid cells or megakaryocytes of the myeloid lineage.

"Isolated" refers to a product, compound, or composition which is separated from at least one other product, compound, or composition with which it is associated in its naturally occurring state, whether in nature or as made synthetically.

"Hematopoietic stem cell" or "HSC" refers to clonogenic, self renewing pluripotent cell capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers.

"Marker phenotyping" refers to identification of markers or antigens on cells for determining its phenotype (e.g., differentiation state and/or cell type). This may be done by immunophenotyping, which uses antibodies that recognize antigens present on a cell. The antibodies may be monoclonal or polyclonal, but are generally chosen to have minimal cross-reactivity with other cell markers. It is to be understood that certain cell differentiation or cell surface markers are unique to the animal species from which the cells are derived, while other cell markers will be common between species. These markers defining equivalent cell types between species are given the same marker identification even though there are species differences in structure (e.g., amino acid sequence). Cell markers include cell surfaces molecules, also referred to in certain situations as cell differentiation (CD) markers, and gene expression markers. The gene expression markers are those sets of expressed genes indicative of the cell type or differentiation state. In part, the gene expression profile will reflect the cell surface markers, although they may include non-cell surface molecules.

"Megakaryocyte/erythroid progenitor cell" or "MEP" refers to a cell derived from common myeloid progenitor cells, and characterized by its capacity to gives rise to erythroid cells and megakaryocytes, but which does not typically give rise to granulocytes, macrophages, or myeloid dendritic cells.

"Mismatched allogeneic" refers to deriving from, originating in, or being members of the same species having non-identical major histocompatability complex (MHC) antigens (i.e., proteins) as typically determined by standard assays used in the art, such as serological or molecular analysis of a defined number of MHC antigens. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

"Myeloablative" or "myeloablation" refers to impairment or destruction of the hematopoietic system, typically by exposure to a cytotoxic agent or radiation. Myeloablation encompasses complete myeloablation brought on by high doses of cytotoxic agent or total body irradiation that destroys the hematopoietic system. It also includes a less than complete myeloablated state caused by non-myeloablative conditioning. Thus, a non-myeloablative conditioning is treatment that does not completely destroy the subject's hematopoietic system.

"Self renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype.

"Sorting" as it pertains to cells refers to separation of cells based on physical characteristics or presence of markers (such as sorting using side scatter (SSC) and forward scatter (FSC), or fluorescence activation cell sorting (FACS) using labeled antibodies), or analysis of cells based on presence of cell markers, e.g., FACS without sorting.

"Substantially pure cell population" refers to a population of cells having a specified cell marker characteristic and differentiation potential that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

"Subject" or "patient" are used interchangeably and refer to, except where indicated, mammals such as humans and non-human primates, as well as rabbits, rats, mice, goats, pigs, and other mammalian species.

"Syngeneic" refers to deriving from, originating in, or being members of the same species that are genetically identical, particularly with respect to antigens or immunological reactions. These include identical twins having matching MHC types. Thus, a "syngeneic transplant" refers to transfer of cells or organs from a donor to a recipient who is genetically identical to the donor.

"Xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

6.2 Enhancing Engraftment of a Hematopoietic Stem Cell Transplant Graft

The present disclosure describes methods, compositions, and kits for facilitating stem cell engraftment. In one aspect, methods are provided for enhancing engraftment of HSC in a patient in need thereof, which comprises administering (MP) cells to the patient. As demonstrated for the first time herein, MP cells enhance engraftment of HSCs and thereby improve the survival of transplant patients receiving an HSC graft, particularly where the HSC graft is suboptimal with respect to cell count and/or HLA mismatch.

Hematopoietic stem cells are pluripotent stem cells capable of self-renewal and are characterized by their ability to give rise under permissive conditions to all cell types of the hematopoietic system. HSC self-renewal refers to the ability of an HSC cell to divide and produce at least one daughter cell with the same self renewal and differentiation potential of a HSC; that is, cell division gives rise to additional HSCs. Self-renewal provides a continual source of undifferentiated stem cells for replenishment of the hematopoietic system. The marker phenotypes useful for identifying HSCs will be those commonly known in the art. For human HSCs, the cell marker phenotypes preferably include $CD34^+$ $CD38^-$ $CD90$ $(Thy1)^+$ $Lin^-$. For mouse HSCs, an exemplary cell marker phenotype is $Sca-1^+$ $CD90^+$ (see, e.g., Spangrude, G. J. et al., *Science* 1:661-673 (1988)) or $c-kit^+$ $Thy^{lo}$ $Lin^-$ $Sca-1^+$ (see, Uchida, N. et al., *J. Clin. Invest.* 101(5):961-966 (1998)). Alternative HSC markers such as aldehyde dehydrogenase (see Storms et al., *Proc. Nat'l Acad. Sci.* 96:9118-23 (1999), AC133 (see Yin et al., *Blood* 90:5002-12 (1997), and CD150 (SLAM) (see Kiel *Cell* 2005, 121(7) 1109-21) may also find advantageous use.

HSCs give rise to committed lymphoid or myeloid progenitor (MP) cells. As used herein committed myeloid progenitor cells refer to cell populations capable of differentiating into any of the terminally differentiated cells of the myeloid lineage. Encompassed within the myeloid progenitor cells are the common myeloid progenitor cells (CMP), a cell population characterized by limited or non-self-renewal capacity but which is capable of cell division to form granulocyte/macrophage progenitor cells (GMP) and megakaryocyte/erythroid progenitor cells (MEP). Non-self renewing cells refers to cells that undergo cell division to produce daughter cells, neither of which have the differentiation potential of the parent cell type, but instead generates differentiated daughter cells. The marker phenotypes useful for identifying CMPs include those commonly known in the art. For CMP cells of murine origin, the cell population is characterized by the marker phenotype c-Kit$^{high}$ (CD117) CD16$^{low}$ CD34$^{low}$ Sca-1$^{neg}$ Lin$^{neg}$ and further characterized by the marker phenotypes FcγR$^{lo}$ IL-7Rα$^{neg}$(CD127). The murine CMP cell population is also characterized by the absence of expression of markers that include B220, CD4, CD8, CD3, Ter119, Gr-1 and Mac-1. For CMP cells of human origin, the cell population is characterized by CD34$^+$CD38$^+$ and further characterized by the marker phenotypes CD123$^+$ (IL-3Rα) CD45RA$^{neg}$. The human CMP cell population is also characterized by the absence of cell markers CD3, CD4, CD7, CD8, CD10, CD11b, CD14, CD19, CD20, CD56, and CD235a. Descriptions of marker phenotypes for various myeloid progenitor cells are described in, for example, U.S. Pat. Nos. 6,465,247 and 6,761,883; Akashi, *Nature* 404: 193-197 (2000), and Manz, *Proc. Natl. Acad. Sci. USA* 99(18): 11872-7 (2002); all publications incorporated herein by reference in their entirety.

Another committed progenitor cell of the myeloid lineage is the granulocyte/macrophage progenitor cell (GMP). The cells of this progenitor cell population are characterized by their capacity to give rise to granulocytes (e.g., basophils, eosinophils, and neutrophils) and macrophages. Similar to other committed progenitor cells, GMPs lack self-renewal capacity. Murine GMPs are characterized by the marker phenotype c-Kit$^{hi}$ (CD117) Sca-1$^{neg}$FcγR$^{hi}$ (CD16) IL-7Rγ$^{neg}$ CD34$^{pos}$. Murine GMPs also lack expression of markers B220, Ter119, CD4, CD8, CD3, Gr-1, Mac-1, and CD90. Human GMPs are characterized by the marker phenotype CD34$^+$ CD38$^+$ CD123+CD45RA$^+$. Human GMP cell populations are also characterized by the absence of markers CD3, CD4, CD7, CD8, CD10, CD11b, CD14, CD19, CD20, CD56, and CD235a.

The megakaryocyte/erythroid progenitor cells (MEP), which are derived from the CMPs, are characterized by their capability of differentiating into committed megakaryocyte progenitor and erythroid progenitor cells. Mature megakaryocytes are polyploid cells that are precursors for formation of platelets, a developmental process regulated by thrombopoietin. Erythroid cells are formed from the committed erythroid progenitor cells through a process regulated by erythropoietin, and ultimately differentiate into mature red blood cells. Murine MEPs are characterized by cell marker phenotype c-Kit$^{hi}$ and IL-7R$^{neg}$ and further characterized by marker phenotypes FcR$^{lo}$ and CD34$^{low}$. Murine MEP cell populations are also characterized by the absence of markers B220, Ter1119, CD4, CD8, CD3, Gr-1, and CD90. Another exemplary marker phenotype for mouse MEPs is c-kit$^{high}$ Sca-1$^{neg}$ neg Lin$^{neg/low}$ CD16$^{low}$ CD34$^{low}$. Human MEPs are characterized by marker phenotypes CD34$^+$ CD38$^+$ CD123$^{neg}$ CD45RA$^{neg}$. Human MEP cell populations are also characterized by the absence of markers CD3, CD4, CD7, CD8, CD10, CD11b, CD14, CD19, CD20, CD56, and CD235a.

Further restricted progenitor cells in the myeloid lineage are the granulocyte progenitor, macrophage progenitor, megakaryocyte progenitor, and erythroid progenitor. Granulocyte progenitor cells are characterized by their capability to differentiate into terminally differentiated granulocytes, including eosinophils, basophils, neutrophils. The GPs typically do not differentiate into other cells of the myeloid lineage. With regards to the megakaryocyte progenitor cell (MKP), these cells are characterized by their capability to differentiate into terminally differentiated megarkaryocyte but generally not other cells of the myeloid lineage (see, e.g., WO 2004/024875).

HSC and MP cells can be obtained from a variety of sources, including bone marrow, peripheral blood, cord blood, and other sources known to harbor hematopoietic and myeloid progenitor cells, including liver, particularly fetal liver. Peripheral and cord blood is a rich source of HSCs and MP cells. Cells are obtained using methods known and commonly practiced in the art. For example, methods for preparing bone marrow cells are described in Sutherland et al., *Bone Marrow Processing and Purging: A Practical Guide* (Gee, A. P. ed.), CRC Press Inc. (1991)). HSC and MP cells can also be derived from primordial stem cell sources such as embryonic stem cells (Thomson et al., *Science* 282:1145 (1998)) and germ cells (Shamblott et al., *Proc. Natl. Acad. Sci. USA* 95:13726 (1998)) using appropriate expansion and differentiation techniques.

The HSC and MP cells are derived from any animal species with a hematopoietic system, as generally described herein. Preferably, suitable animals will be mammals, including, by way of example and not limitation, rodents, rabbits, canines, felines, pigs, horses, cows, primates (e.g., human), and the like.

In some embodiments, expanded stem cell populations can be used. Stem cells can be expanded in distinct media compositions comprising a mixture of cytokines. The expanded stem cell population is not to be construed or limited by any mechanism or theory of cellular origin and may comprise cells grown in culture, and cells that increase in expression of the CD34 antigen, or combinations thereof. Stem cell expansion techniques are known in the art, including, U.S. Pat. No. 6,326,198, U.S. Pat. No. 6,338,942; U.S. Pat. No. 6,335,195, which are hereby incorporated by reference in their entireties.

In some embodiments, expanded MP populations can be used. MP can be expanded in distinct media compositions comprising a mixture of cytokines. The expanded MP population is not to be construed or limited by any mechanism or theory of cellular origin and may comprise cells grown in culture, and cells that increase in expression of the CD34 antigen, or combinations thereof. MP expansion techniques are known in the art, including, for example, co-pending U.S. patent application Ser. No. 11/259,592, entitled Methods of Expanding Myeloid Cell Populations and Uses Thereof, and U.S. Pat. No. 6,967,029, which are hereby incorporated by reference in their entireties.

The subject invention is applicable to autologous or allogeneic HSC transplants. Accordingly, in one embodiment, the method provides enhanced engraftment of an autologous HSC graft by administering MP cells, wherein the MP cells can be autologous or allogeneic with respect to the HSC graft or to the patient, as demonstrated herein. In other embodiments, the method provides enhanced engraftment of an allogeneic HSC graft by administering MP cells, wherein the MP cells can be autologous or allogeneic with respect to to the HSC graft or host, as demonstrated herein. Thus, the present inventors have determined that the HSC and MP cells employed in the subject methods may be completely matched, partially mismatched allogeneic, and/or fully mismatched allogeneic cells with respect to the MHC of the HSC graft as well as to the transplant recipient, and may be from related donors, usually siblings with the same parental alleles, or unrelated donors.

The HSC and MP cells may also be subjected to further selection and purification, which can include both positive and negative selection methods, to obtain a substantially pure population of cells. In one aspect, fluorescence activated cell sorting (FACS), also referred to as flow cytometry, is used to sort and analyze different cell populations. Cells having the cellular markers specific for HSC or MP cell populations are tagged with an antibody, or typically a mixture of antibodies, that bind the cellular markers. Each antibody directed to a different marker is conjugated to a detectable molecule, particularly a fluorescent dye that can be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and progenitor cells is described in, among others, U.S. Pat. Nos. 5,137,809, 5,750,397, 5,840,580; 6,465,249; Manz, M. G. et al., *Proc. Natl. Acad. Sci. USA* 99:11872-11877 (2002); and Akashi, K. et al., *Nature* 404 (6774):193-197 (2000)). General guidance on fluorescence activated cell sorting is described in, for example, Shapiro, H. M., *Practical Flow Cytometry*, 4th Ed., Wiley-Liss (2003) and Ormerod, M. G., *Flow Cytometry: A Practical Approach*, 3rd Ed., Oxford University Press (2000).

It is to be understood that the purification of cells also includes combinations of the methods described herein. A typical combination may comprise an initial procedure that is effective in removing the bulk of unwanted cells and cellular material, for example leukapharesis. A second step may include isolation of cells expressing a marker common to one or more of the progenitor cell populations by immunoadsorption on antibodies bound to a substrate. For example, magnetic beads containing anti-CD34 antibodies are able to bind and capture HSC, CMP, and GMP cells that commonly express the CD34 antigen. An additional step providing higher resolution of different cell types, such as FACS sorting with antibodies to a set of specific cellular markers, can be used to obtain substantially pure populations of the desired cells. Another combination may involve an initial separation using magnetic beads bound with anti-CD34 antibodies followed by an additional round of purification with FACS.

The amount of the cells needed for achieving a therapeutic effect will be determined empirically in accordance with conventional procedures for the particular purpose. Generally, for administering cells for therapeutic purposes, the cells are given at a pharmacologically effective dose. By "pharmacologically effective amount" or "pharmacologically effective dose" is an amount sufficient to produce the desired physiological effect or amount capable of achieving the desired result, particularly for engraftment or survival of a subject. Therapeutic benefit also includes halting or slowing the progression of the underlying disease or disorder, regardless of whether improvement is realized. Pharmacologically effective dose, as defined above, will also apply to therapeutic compounds used in combination with the cells, as further described below.

The stem cell transplant graft can vary widely as a function of the age, weight and state of health of the patient, the nature and the severity of the indication. Suitable dosage ranges for the HSCs vary according to these considerations.

An optimal HSC graft requires a threshold number of cells/kg patient in order to achieve a successful stem cell transplantation. According to the published data and conclusions from recent clinical studies, an optimal HSC graft should generally contain at least about $1.0 \times 10^6$ CD34+ cells per kg/patient, at least about $2.0 \times 10^6$ CD34+ cells per kg/patient, preferably at least about $3.0 \times 10^6$ CD34+ cells per kg/patient, more preferably at least about $4.0 \times 10^6$ CD34+ cells per kg/patient, and most preferably greater than $5.0 \times 10^6$ CD34+ cells per kg/patient. See, e.g., Olivieri, A. et al. (1998) *Haematologica*, 83:329-337; Mavroudis, D. et al. (1996) *Blood*, Vo. 88, No. 8 (October 15); pp 3223-3229; Singhal, S. et al. (2000) *Bone Marrow Transplantation*, 26, 489-96; Bittencourt, H. et al. (2002) *Blood*, Vol. 99, No. 8 (April 15); 2726-2733).

In a preferred aspect, the subject methods and compositions find use with grafts having less than an optimal HSC dose, e.g., a dose resulting in less than median therapeutic benefit, as determined by methods known in the art. In some embodiments, the administration of MP cells enhances engraftment of a suboptimal dose of hematopoietic stems cells. In some embodiments, the survival of a subject can be increased by administrating MP cells in conjunction with a suboptimal dose of hematopoietic stems cells. In such methods, the administration of MP to a patient in conjunction with a suboptimal graft results in an overall improvement in effectiveness of treatment.

Accordingly, in one aspect, the methods of the present invention employ MP grafts in conjunction with suboptimal HSC grafts, which will generally comprise less than about $5.0 \times 10^6$ CD34+ cells per kg/patient, more specifically less than about $4.0 \times 10^6$ CD34+ cells per kg/patient, preferably less than about $3.0 \times 10^6$ CD34+ cells per kg/patient, more preferably less than about $2.0 \times 10^6$ CD34+ cells per kg/patient, or most preferably less than about $1.0 \times 10^6$ CD34+ cells per kg/patient.

A cord blood unit is the blood collected from a single placenta and umbilical cord. The number of nucleated cells in a cord blood unit varies. In addition, the number of nucleated cells in a cord blood unit may be less after freezing and thawing. Thus, in administering HSCs, it is instructive to note whether nucleated cell count was measured before or after thawing the unit. In some embodiments, the suboptimal graft comprises less than two cord blood units. In some embodiments, the suboptimal graft comprises a single cord blood unit.

In some embodiments, a suboptimal graft is function of nucleated cells (NC) per kg patient body weight administered to a patient. In one embodiment, a suboptimal UCB graft for infusion is about $4 \times 10^7$ nucleated cells/kg patient. In one embodiment, a suboptimal UCB graft is less than $3 \times 10^7$ nucleated cells/kg patient, and preferably less than about $3.5 \times 10^7$ nucleated cells/kg patient. In one embodiment, a suboptimal UCB graft for infusion is about 2 or $2.5 \times 10^7$ nucleated cells/kg patient.

The threshold cell count for optimal HSC grafts from bone marrow or peripheral blood sources are generally about a magnitude greater than those for UCB grafts. In one embodiment, a suboptimal graft for infusion from these sources is about $5 \times 10^8$ nucleated cells/kg patient. In one embodiment, a suboptimal graft is less than 4 or $4.5 \times 10^8$ nucleated cells/kg patient, and preferably less than about $4.1 \times 10^8$ nucleated cells/kg patient. In one embodiment, a suboptimal graft is less than about 3 or $3.5 \times 10^8$ nucleated cells/kg patient.

In some embodiments, a suboptimal graft is a function of the number of $CD34^+$ cells administered to a patient. In one embodiment, a suboptimal UCB graft for infusion is less than about $5 \times 10^5$ $CD34^+$ cells/kg patient. In one embodiment, a suboptimal UCB graft for infusion is less than about 3.5 to $4.5 \times 10^5$ $CD34^+$ cells/kg patient, and preferably less than about $4 \times 10^5$ $CD34^+$ cells/kg patient. In one embodiment, a suboptimal UCB graft for infusion is less than about $3 \times 10^5$ CD34+ cells/kg of patient.

The threshold cell count for optimal HSC grafts from bone marrow or peripheral blood sources are generally about a magnitude greater than those for UCB grafts. In one embodiment, a suboptimal graft for infusion from these sources is less than about $5 \times 10^6$ $CD34^+$ cells/kg patient. In one embodiment, a suboptimal graft for infusion is less than about $4 \times 10^6$ $CD34^+$ cells/kg patient, and preferably less than about $3 \times 10^6$ $CD34^+$ cells/kg patient.

In one embodiment, a suboptimal graft for infusion is less than about 2 or $1 \times 10^6$ CD34+ cells/kg of patient.

In some embodiments, a suboptimal graft is function of mismatch at the MHC, for example, a suboptimal graft can be from a partially- or fully-mismatched allogeneic donor. In some embodiments, a suboptimal graft is at least partially mismatched at one MHC locus with respect to the patient. In one embodiment, the suboptimal graft is mismatched with respect to one or more antigens. In one embodiment, the suboptimal graft is mismatched at the MHC with respect to at least two antigens. The antigens may be within the same MHC locus or different MHC loci.

Determining the degree of MHC mismatch will employ standard tests known and used in the art. For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests are made of at least 4, and preferably at least 6 MLC antigens within the two or three HLA groups, respectively.

In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis (i.e., lymphocytotoxicity testing). The reaction is examined and graded according to the amount of cells lysed in the reaction (Mickelson, E. and Petersdorf, E. W., *Hematopoietic Cell Transplantation*, Thomas, E. D. et al. eds., pg 28-37, Blackwell Scientific, Malden, Mass. (1999). Other cell-based assays include flow cytometry using labeled antibodies or enzyme linked immuno assays (ELISA).

Molecular methods for determining MHC type generally employ synthetic probes and/or primers to detect specific gene sequences that encode the HLA protein. Synthetic oligonucleotides may be used as hybridization probes to detect restriction fragment length polymorphisms associated with particular HLA types (Vaughn, R. W., *Methods in Molecular Biology: MHC Protocols* 210:45-60 (2002)). Alternatively, primers may be used for amplifying the HLA sequences (e.g., by polymerase chain reaction or ligation chain reaction), the products of which can be further examined by direct DNA sequencing, restriction fragment polymorphism analysis (RFLP), or hybridization with a series of sequence specific oligonucleotide primers (SSOP) (Petersdorf, E. W. et al., *Blood* 92(10):3515-20 (1998); Morishima, Y. et al., *Blood* 99(11):4200-6 (2002); and Middleton, D. and Williams, F., *Methods in Molecular Biology: MHC Protocols* 210:67-112 (2002)).

Although a suboptimal graft may determined as described above, the present disclosure is not limited to such a metric. Alternative metrics are know to one of skill in the art. For example, a suboptimal graft can determined by the number of colony forming cells, the number of granulocyte-macrophage colony forming cells, the number of burst forming unit-erythroid cells, or the number of colony forming unit-granulocyte erythroid monocyte macrophage cells, that are collected, thawed, or administered, for example.

Generally, for administering MP cells for therapeutic purposes, the cells are given at a pharmacologically effective dose. By "pharmacologically effective amount" or "pharmacologically effective dose" is an amount sufficient to produce the desired physiological effect or amount capable of achieving the desired result, particularly for treating the disorder or disease condition, including reducing or eliminating one or more symptoms or manifestations of the disorder or disease. Therapeutic benefit also includes halting or slowing the progression of the underlying disease or disorder, regardless of whether improvement is realized.

The amount of the MP cells needed for achieving a therapeutic effect can be determined empirically in accordance with conventional procedures for the particular purpose. The amount of the MP cells can vary widely as a function of the age, weight and state of health of the patient, the nature and the severity of the indication. In addition, the amount of MP cells administered can vary with stem cell transplant graft, but in general, the amount of MP cells is administered in amount to enhance HSC engraftment. In some embodiments, the amount of MP cells is administered in amount to increase patient survival.

In some embodiments, the numbers of MP cells infused may be from about $1 \times 10^5$ to about $1 \times 10^9$ cells/kg, more preferably from about $1 \times 10^6$ to about $1 \times 10^8$ cells/kg, and most preferably about $1 \times 10^7$ cells/kg of body weight, or more as necessary.

Transplantation of cells into patient is accomplished by methods generally used in the art. The preferred method of administration is intravenous infusion. As described above, the number of cells transfused will take into consideration factors such as sex, age, weight, the types of disease or disorder, stage of the disorder, the percentage of the desired cells in the cell population (e.g., purity of cell population), and the cell number needed to produce a therapeutic benefit.

Cells can be administered in one infusion, or through successive infusions over a defined time period sufficient to generate a therapeutic effect. Different populations of cells may be infused when treatment involves successive infusions. A pharmaceutically acceptable carrier, as further described below, may be used for infusion of the cells into the patient. These will typically comprise, for example, buffered saline (e.g., phosphate buffered saline) or unsupplemented basal cell culture medium, or medium as known in the art. In some embodiments, MP cells can be used concurrently, subsequent, or prior to stem cell transplantation.

The methods of enhancing engraftment of a hematopoietic stem cell transplant graft administering myeloid progenitor cells can be used for treatment of various disorders. In some embodiments, the disorder relates to deficiencies in hematopoiesis caused by disease or myeloablative treatments. As used herein, "treatment" refers to therapeutic or prophylactic treatment, or a suppressive measure for the disease, disorder or undesirable condition. Treatment encompasses administration of the subject cells in an appropriate form prior to the onset of disease symptoms and/or after clinical manifestations, or other manifestations of the disease or condition to reduce disease severity, halt disease progression, or eliminate the disease. Prevention of the disease includes prolonging or delaying the onset of symptoms of the disorder or disease, preferably in a subject with increased susceptibility to the disorder.

The disclosure further provides the use of MP cells to enhance engraftment of a hematopoietic stem cell transplant graft in the field of solid organ, cell, or tissue transplantation. By way of example, but not as a limitation, the disclosure further provides use of MP cells to enhance engraftment of a hematopoietic stem cell transplant graft in the transplant of heart, lung liver, kidney, islet cells, skin, endocrine organs, or pancreas.

6.3 Adjunctive Treatments

A variety of adjunctive treatments may be used with the methods described herein. In one aspect, the adjunctive treatments include, among others, anti-fungal agents, anti-bacterial agents, and anti-viral agents.

In one aspect, the adjunctively administered agent is an anti-fungal agent. Fungal infections are a significant problem in patients who have undergone myeloablative therapy and HSCT. Recipients with delayed engraftment and patients who develop GVHD typically are at high risk for fungal infections. Types of fungal infections are varied, and include, among others, candidiasis (e.g., with *candida krusei, candida glabrata, candida albicans, candida tropicalis*), aspergillosis (e.g., with *aspergillus fumigatus, aspergillus flavus*), mucormycosis (e.g., with *rhizobium arrhizus, absidia corymbifera, rhizomucor pusillus*), cryptococcosis, *histoplasma capsulatum*, and *coccidioides immitis*.

Anti-fungal agents for adjunctive administration will generally be a systemic antifungal agent. One useful antifungal agent of this type is amphotericin B from the family of polyene macrolide antibiotics. Amphotericin B is available in various formulations, including as a complex with deoxycholate; in a colloidal suspension with cholestearyl sulfate; and encapsulated in liposomes made of soy lecithin, cholesterol, and distearoylphosphatidylglycerol, other formulations are known in the art.

Another antifungal agent is flucytosine, a fluorinated pyrimidine. Deamination of flucytosine by the fungus generates 5-fluorouracil, an anti-metabolite and DNA synthesis inhibitor. Flucytosine is typically used for infections of *cryptococcus* and candiadosis. Although used alone, flycytosine is generally used in combination with amphotericin B.

Imidazoles and triazoles represent a broad class of azole based antifungal agents. It is believed that imidazoles and triazoles inhibit sterol 14-α-demethylase, resulting in impaired biosynthesis of ergosterol and disruption of cell membrane based activities, such as electron transport. Azole based anti-fungals are effective against certain types of candiadosis, such as *candida albicans, candida glabrata*, and *candida neoformans*. Exemplary azole antifungals suitable for systemic administration include, among others, ketoconzaole, itracanazole, fluconazole, econazole, voriconazole, and tercanozole.

In addition to fungal infections, a patient with neutropenia is susceptible to infection with a variety of bacterial pathogens. Patients undergoing myeloablative regimens and HSCT have high rates of bacterial infection with both Gram positive (e.g., *streptococcus* and *staphylococcus aureus*) and Gram negative bacteria (e.g., *E. coli.* and *pseudomonas aeruginosa*). Septecemia is a common occurrence. In addition, delayed engraftment and impaired restoration of immune responses against encapsulated bacteria, such as *streptococcus pneumoniae* or *haemophilus influenza*, increases the morbidity rate for transplant recipients with GVHD.

Adjunctive antibacterial therapy can use any known antibiotics suitable for the particular bacterial pathogen. These include both wide spectrum antibiotics and more targeted anti-bacterial compounds. Various classes of anti-bacterial agents suitable with the expanded myeloid cells include, by way of example and not limitation, quinolones and fluoroquinolones, β-lactam antibiotics, aminoglycosides, tetracyclins, macrolides, and various cogeners thereof. Exemplary quinolone compounds include ciprofloxacin, ofloxacin, sparfloxacin, lomefloxacin, and moxifloxacin. Exemplary β-lactam antibiotics include penicillins (e.g., penicillin G, penicillin V), ampicillin, carbenicillin, methicillin, carbapenem, and cephalosporins (e.g., cephalothin, cefamandole, cefaclor, cefonicid, cefotetan, cefatoxime, ceftazidime, ceftizoxime, cefepime). Exemplary aminoglycosides include neomycin, streptomycin, kanamycin, gentamicin, tobramycin, amikacin, and netilmicin. Exemplary macrolides include erythromycin, clarithromycin, and azithromycin. Other antibiotics will be apparent to the skilled artisan.

Viral infections are also problematic in myeloablated patients and HSCTs. Generally the increased risk of viral infection results from impaired cell mediated immunity brought on by the myeloablative therapy. Many of these infections arise from reactivation of latent virus existing in a seropositive patient or in the cells of a seropositive donor. Viruses commonly encountered include, among others, cytomegalovirus, herpes simplex virus, varicella zoster virus, herepesvirus-6, Epstein Barr virus; adenoviruses, and the like. As an adjunct to the cell infusions, anti-viral compounds selected are those appropriate to the viruses encountered by the patient. Useful antiviral compounds include, by way of example and not limitation, acyclovir, cidofovir, ganciclovir, idoxuridine, penciclovir, valganciclovir, valacyclovir, vidarabine, amantadine, rimantadine, zanamivir, fomivirsen, imiquimod, and ribavirin. Therapeutics directed against retroviruses include, among others, nucleoside reverse transcriptatse inhibitors (e.g., zidovudine, didanosine, stavudine, zalcitabine, lamividudine), non-nucleoside reverse transcriptase inhibitors (e.g., nevirapine, efavirenz, delvirudine), and protease inhibitors (e.g., saquinivir, indinavir, ritonavir, nelfinavir, amprenavir, and lopinavir).

The antifungal, antibacterial, and antiviral agents may be used as prophylaxis to reduce the occurrence of the infection, or upon appearance of the disease. Prophylaxis is particularly indicated for fungal infections common in immunosuppressed patients, and for viral infections in seropositive patients or seropositive transplant donors. Accordingly, embodiments for therapeutic purposes include combinations of HSC, MP cells and the antifungal, antibacterial, or antiviral compounds.

In a further embodiment, the adjunctively administered agent is a cytokine or growth factor that enhances differentiation and mobilization of terminally differentiated myeloid cells, particularly granulocytes, macrophages, megakaryocytes and erythroid cells. For enhancing granulocyte development, the cytokines C-CSF and GM-CSF may be used. G-CSF is effective in accelerating engraftment and production of neutrophils in HSCT. In another embodiment, the cytokine or growth factor is thrombopoietin. Administration of TPO enhances engraftment of transplanted progenitor cells and promotes development of megakaryocytes and platelets (Fox, N et al., *J. Clin. Invest.* 110:389-394 (2002); Akahori, H. et al., *Stem Cells* 14(6):678-689 (1996)).

A variety of vehicles and excipients and routes of administration may be used for adjunctive therapy, as will be apparent to the skilled artisan. Representative formulation technology is taught in, inter alia, *Remington: The Science and Practice of Pharmacy*, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the compounds, or mixture of thereof, or suitable salts thereof. The pharmaceutical composition may be formulated as powders, granules, solutions, suspensions, aerosols, solids, pills, tablets, capsules, gels, topical cremes, suppositories, transdermal patches, and other formulations known in the art.

As used herein, "pharmaceutically acceptable carrier" comprises any of standard pharmaceutically accepted carriers known to those of ordinary skill in the art in formulating pharmaceutical compositions. Thus, the compounds, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

While any suitable carrier known to those of ordinary skill in the art may be employed in the compositions, the type of carrier will typically vary depending on the mode of administration. The therapeutic compositions may be formulated for any appropriate manner of administration, including for example, oral, nasal, mucosal, rectal, vaginal, topical, intravenous, intraperitoneal, intradermal, subcutaneous, and intramuscular administration.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above. Alternatively, a pharmaceutical composition may be stored in a freeze-dried condition requiring only the addition of a sterile liquid carrier immediately prior to use.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease.

Determining the dosages and times of administration for a therapeutically effective amount are well within the skill of the ordinary person in the art. For example, an initial effective dose can be estimated from cell culture or other in vitro assays. A dose can then be formulated in animal models to generate a circulating concentration or tissue concentration, including that of the $IC_{50}$ as determined by the cell culture assays.

6.4 Kits

The methods described herein can be facilitated by a kits for enhancing HSC engraftment. The kits may contain cells including but not limited to HSCs, MPs, including expanded and or isolated cells, and/or adjunctive therapeutic compounds, means for isolating or expanding HSCs and MPs, means for administering cells to a patient, or any combination thereof. The kits may optionally comprise any or all of a pharmaceutically acceptable carrier, a physiologically acceptable carrier, instructions for use, a container, a vessel for administration, antibodies, or any combination thereof. A label typically accompanies the kit, and includes any writing or recorded material, which may be electronic or computer readable form (e.g., disk, optical disc, memory chip, or tape) providing instructions or other information for use of the kit contents.

7. EXAMPLES

Aspects of the present teachings may be further understood in light of the following examples, which should not be construed as limiting the scope of the present teachings in any way.

7.1 Example 1

Experimental Methods

Preparation of Hsc or Mp from Mice.

For Obtaining Mouse Bone Marrow Cells, animals are euthanized and the femur/tibia removed and cleaned of muscle. The bones are crushed into a pulp using a pestle and mortar, the marrow filtered through nylon screen, and then centrifuged at 1200 RPM for 5 minutes. Cells are resuspended in 1 ml ACK solution (0.3M NH$_4$Cl, 0.2M KHCO$_3$, MiliQ filtered water) for 3-4 minutes on ice, and then washed by filling the tube with staining media (HANKs buffered saline containing 2% FCS and 2 mM EDTA, w/o calcium, w/o magnesium, w/o phenol red). Cells are centrifuged, filtered, and resuspended in staining media, and mouse IgG (1:50 dilution of a 1 mg/ml stock, Sigma, St Louis Mo.) are added. Cells are incubated on ice for 10-15 minutes and then mixed with CD117 microbeads (Miltenyi Biotech, Auburn Calif.) at a volume of 10 μl/mouse in a final volume of 100 μl/mouse in staining media. Cells are incubated on ice for 25 minutes. Cells are washed, resuspended in staining media at a final volume ~1 ml/mouse, and filtered through a nylon screen. Cells are enriched using an AutoMACs (Miltenyi, Auburn, Calif.), according to manufacturer's directions using the posselds setting. Following enrichment, cells are resuspended at about 1×10$^8$ cells/ml in staining media with the following directed conjugated antibodies (ebioscience, San Diego, Calif.) added at the appropriate concentration: Sca-1 allophycocyanin (APC), c-kit R-phycoerythrin-cyanine 7 tandem (PE-Cy7), Thy-1.1 fluorescein isothiocyanate (FITC), lineage (CD3, CD4, CD5, CD8, B220, mac-1, Gr-1, and Ter119) R-phycoerythrin (PE). Cells are incubated on ice for 25 minutes, washed, centrifuged, and resuspended in staining media. Propidium iodide (PI) is added to exclude dead cells. Mouse KTLS-HSC, c-kit$^{high}$Thy$^{low}$Sca-1$^{pos}$lineage$^{neg}$ or mouse MP c-kit$^{high}$Thy$^{neg}$Sca-1$^{neg}$lineage$^{neg/low}$ are isolated by FACS.

Cell Culture and Expansion.

Lin$^{deg/low}$ KTLS-HSC are sorted from AKR mice (H2Kk) and plated in 500 μl/well serum-free medium containing the cytokine and growth factor combination c-KitL, FL, TPO and IL-6 (X-Vivo15 basal medium (Cambrex Bioscience, MD); penstrep (100×), glutamax (100×), 2-mercaptoethanol (5×10$^{-5}$M), c-KitL (50 ng/ml), FL (30 ng/ml), TPO (5 ng/ml), and IL-6 (10 ng/ml) (Biosource, Camarillo, Calif. and R & D Systems, Minneapolis, Minn.). The cells are plated at about 10,000 cells/well in 24 well plates. The cells are cultured for 7 days to obtain MPc (culture-derived MP). Cells are fed with 500 μl/well on day 2, and on day 4 half of the media is replaced with fresh media. On day 5, cells are transferred to 6 well plates with an addition of 1 ml fresh media. On day 7, the cultured cells are collected and three small aliquots are removed for analysis.

Staining for Mouse HSC in Expanded Cell Populations:

Cells are removed from each well, washed and then transferred to a corresponding conical FACS tube and counted by hemacytometer. Cells are centrifuged for 5 min @ 1100 rpm, and the supernatant removed. 50 μl of blocking antibody (rat IgG and Mouse IgG 1:50) is added, incubated for 10 minutes, followed by 50-100 μl of antibody solution using appropriate concentrations of the following antibodies (eBioscience, San Diego, Calif.): Sca-1 allophycocyanin (APC), Thy-1.1 fluorescein isothiocyanate (FITC), c-kit phycoerythrin-cyanine 7 tandem (PE-Cy7), B220, Mac-1, GR-1 R-phycoerythrin (PE). Following incubation on ice for 25 minutes, cell are washed, centrifuged, and resuspended in staining media containing PI. Cells are analyzed for HSC by FACS.

Staining for Myeloid Progenitors in Culture Expanded Cell Populations:

Cells are prepared in the same manner as done for staining of HSC cells described above. After incubation with 50 μl of blocking antibody (rat IgG and Mouse IgG 1:50), 50-100 μl of lineage-biotin (Ter119, Gr-1, B220) is added to each tube, followed by 20 minutes on ice. Cells are washed with 2-3 ml SM, centrifuged, and then resuspended in 50-100 μl of antibody solution at appropriate concentrations: Streptavidin Cascade Blue (Molecular Probes, Eugene, Oreg.), c-kit phycoerythrin-cyanine 7 tandem (PE-Cy7), Sca-1 allophycocyanin (APC), CD34 fluorescein isothiocyanate (FITC), 2.4G2 (FcγR) R-phycoerythrin (eBioscience, San Diego, Calif.). Cells are analyzed for MP (CMP, GMP, MEP) by FACS.

Staining Culture Expanded Cells for Mature Progenitor Cell Subsets:

Cells are processed as described above. Following incubation with blocking antibody, cells are resuspended in 50-100 μl of antibody solution: CD3 phycoerythrin-cyanine 7 tandem (PE-Cy7), B220 pacific blue, Gr-1R-phycoerythrin (PE) and Mac-1 allophycocyanin (APC), (eBioscience, San Diego, Calif.)). Following incubation on ice for 25 min, cells are processed for FACS analysis as described previously.

Screening Reconstituted Mice for Presence of Donor Cells.

Screening of mice transplanted with HSC's and/or MP's for donor cell population is done by collecting approximately 10-15 drops of blood in 0.5 ml 5 mM EDTA in PBS at room temperature. One ml of 2% dextran-500 in PBS is added, mixed, and incubated at 37° C. for 30-45 min. Most red blood cells will settle. The resulting supernatant is transferred to a new tube, the cells collected by centrifugation (5 min, 1000 rpm), and the remaining red blood cells lysed with 1.0 ml of 1×ACK (0.3M NH4Cl, 0.2M KHCO3, MiliQ filtered water) for 5-6 minutes on ice. This is followed by a wash and centrifugation for 5 minutes at 1200 rpm. If the pellet is still red, the wash steps are repeated. Cells are blocked with rat IgG and mouse IgG (1:50 each) in 50 μl/tube for 10 to 15 minutes on ice. Biotinylated Mac-1 and GR-1 (eBioscience, San Deigo, Calif.) are added at the appropriate concentration, and incubated on ice in the dark for 20 minutes. Cells are washed and centrifuged for 5 minutes at 1200 rpm. The following antibodies are added at the appropriate concentrations for the syngeneic or MUD transplants (C57B6/Ka, CD45.1; C57B16/Ka CD45.2 or 129) Streptaviden Cascade Blue (Molecular Probes, Eugene, Oreg.), CD45.1 allophycocyanin (APC), CD45.2 fluorescein isothiocyanate (FITC), B220 R-phycoerythrin cyanine tandom (PE-Cy7) and CD3, CD4, CD8 R-phycoerythrin (PE) (eBioscience, San Diego, Calif.). The following antibodies are added at the appropriate concentrations for the allogeneic transplants (C57B6/Ka, H2 Kb; Balb/b, H2 Kd) Streptaviden Cascade Blue (Molecular Probes, Eugene, Oreg.), CD3 allophycocyanin (APC), H2 Kb fluorescein isothiocyanate (FITC), B220 R-phycoerythrin cyanine tandom (PE-Cy7) and H2 Kd R-phycoerythrin (PE) (eBioscience, San Diego, Calif.). The following antibodies are added at the appropriate concentrations for the MUD transplants with the cultured allogeneic MP (C57B6/Ka, CD45.1; 129, CD45.2; AKR, H2Kk) CD45.2 biotin (eBioscience, San Diego, Calif.). After washing, the following antibodies are added at the appropriate concentrations, Streptaviden R-phycoerythrin tandom (PE-Cy5), CD45.1 allophycocyanin (APC), H2Kk fluorescein isothiocyanate (FITC), Mac-1 and Gr-1 R-phycoerythrin cyanine tandom (PE-Cy7), B220 Pacific Blue and CD3 R-phycoerythrin (PE) (eBioscience, San Diego, Calif.). Following 25 minute incubation on ice, cells are washed, centrifuged, and resuspended in SM containing PI. Cells are analyzed by FACS.

Freezing of Culture-Derived MP:

Cells are frozen at a concentration of 20 million cells/ml. Prepare freezing media containing 85% FCS and 15% DMSO. Count and wash the culture-derived MP cells. Centrifuge at 1100 RPM. Resuspend the cell pellet at 10 million cells/ml. Slowly, in a drop wise fashion add an equal volume of the DMSO freezing medium, while gently mixing the tube. Aliquot the cells to 1 ml per vial into cryovials. Freeze the cells overnight at −80° C. The next day transfer the vials to liquid nitrogen for long-term storage.

7.2 Example 2

Use of Purified Myeloid Progenitors Cells to Augment Survival in Conjunction with Sub-Optimal Doses of HSC These studies were designed to determine whether MPs could improve survival in cases in which HSCs were provided in inadequate numbers to provide radioprotection in 100% of the recipient mice. These studies investigated whether MPs could augment recovery following purified HSC transplantation in the syngeneic (FIG. 3), matched unrelated donor (MUD) (FIG. 4) or completely mismatched allogeneic settings (FIG. 5). In these studies the HSC and MP for each study were derived from the same donor.

Figures 1A, 1B:
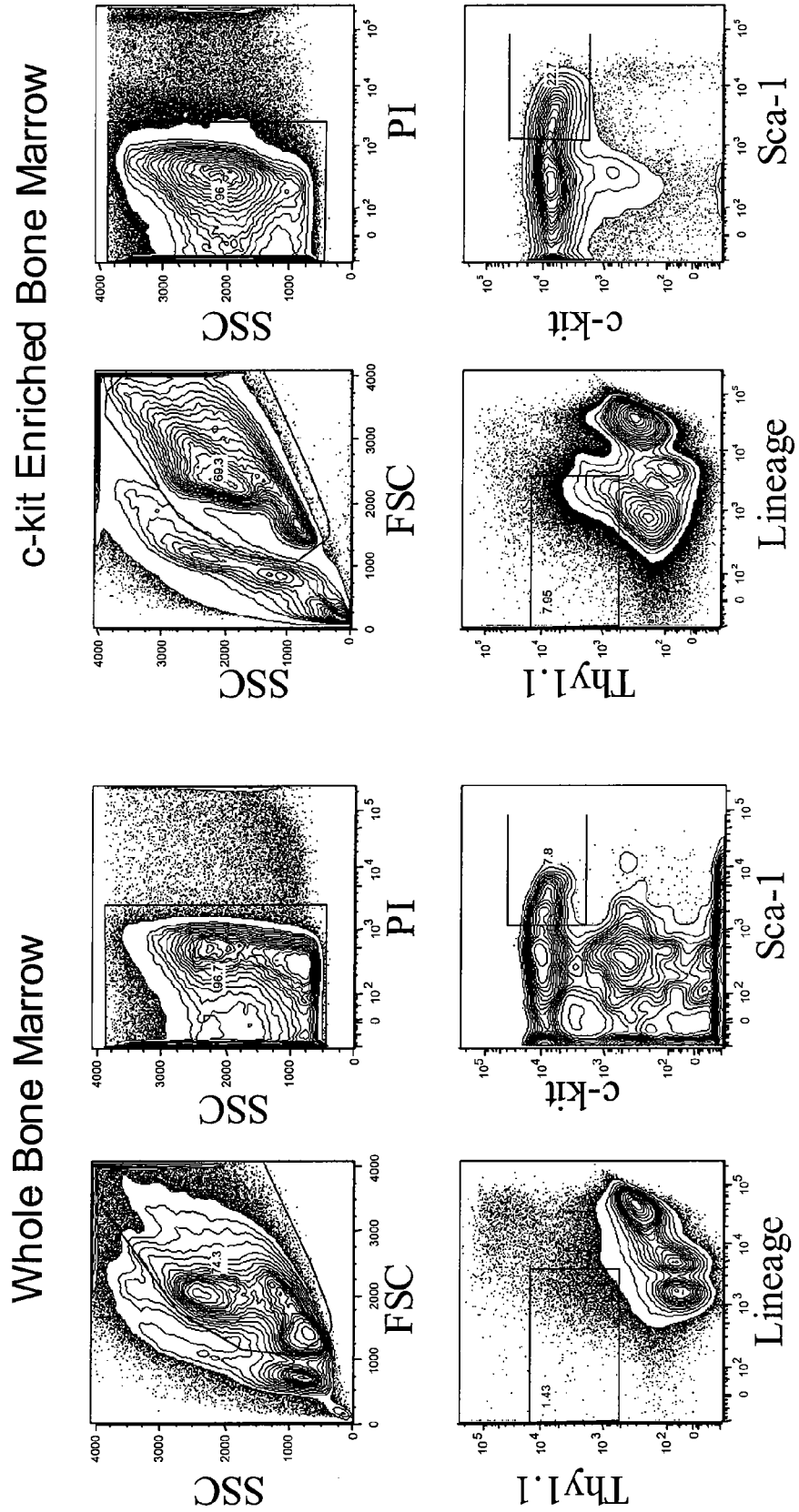
FIG. 1 shows the sort gates for KTLS HSC from C57B6/Ka (Thy-1.1, CD45.2).

HSC were prepared from mouse bone marrow (BM), and $Lin^{neg}$ KTLS-HSCs were sorted from C57B1/6 KA mice (H-2b, CD90.1, CD45.2). FIG. 1 shows the sort gates for KTLS HSC from C57B6/Ka (Thy-1.1, CD45.2). Gating profile is shown for both whole bone marrow and after c-kit enrichment. HSC sorted with this gating strategy were used in the transplantation experiments.

Figures 2A, 2B:
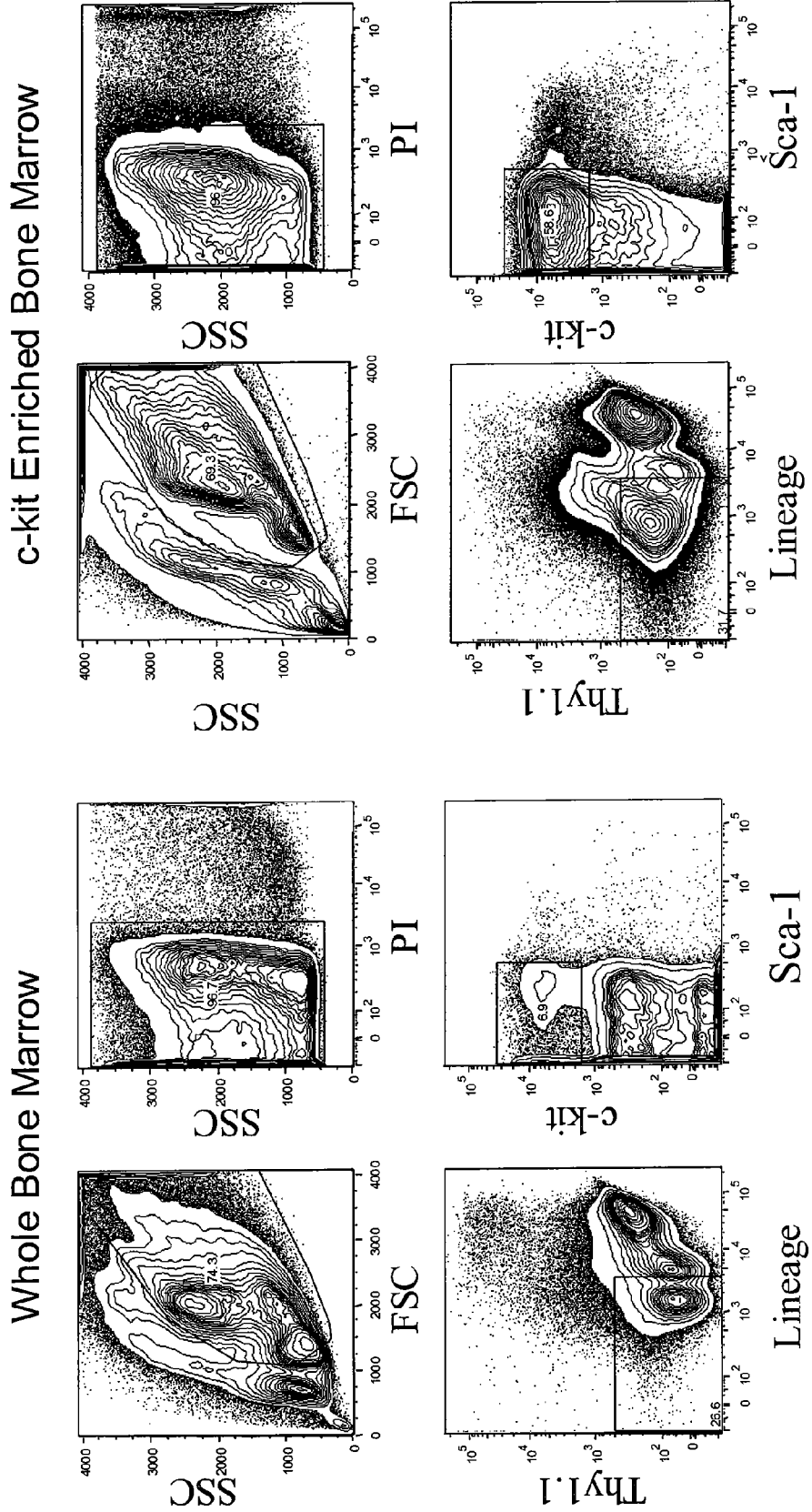
FIG. 2 shows the sort gates for MP from C57B6/Ka (Thy-1.1, CD45.2).

MP were prepared from mouse bone marrow (BM) were sorted from C57B1/6 KA mice (H-2b, CD90.1, CD45.2). FIG. 2 shows the sort gates for MP from C57B6/Ka (Thy-1.1, CD45.2). Gating profile is shown for both whole bone marrow and after c-kit enrichment. MP sorted with this gating strategy were used in the transplantation experiments.

Host-mice, C57Bl/Ka (H-2b, CD90.1, CD45.1), 129 (H-2b, CD45.2) or Balb/c (H-2d, CD45.2) were lethally irradiated using split dose irradiation (9-11Gy total, cesium source) at day 0, Sorted HSC and MP were combined at the desired dose and injected by retro-orbital injection into the recipient animal. Animals were monitored for survival and donor chimerism.

Figure 3:
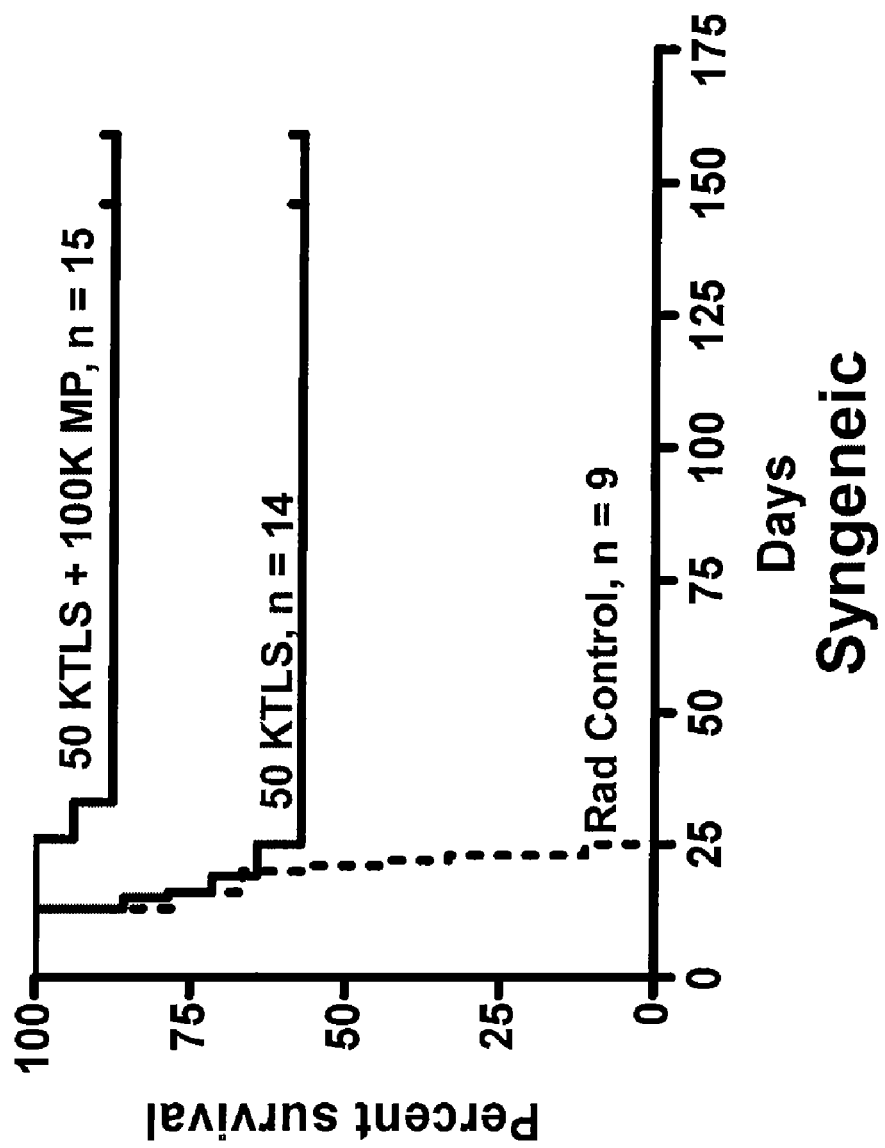
FIG. 3 shows survival data in the syngeneic transplant model.

FIG. 3 shows survival data in the syngeneic transplant model. 50 KTLS C57B6/Ka (Thy-1.1, CD45.2) HSC were transplanted alone or in combination with 100,000 C57B6/Ka (Thy-1.1, CD45.2) MP into C57B6/Ka (Thy-1.1, CD45.1) hosts. FIG. 3 shows the addition of MP to the HSC graft improved survival.

Figure 4B:
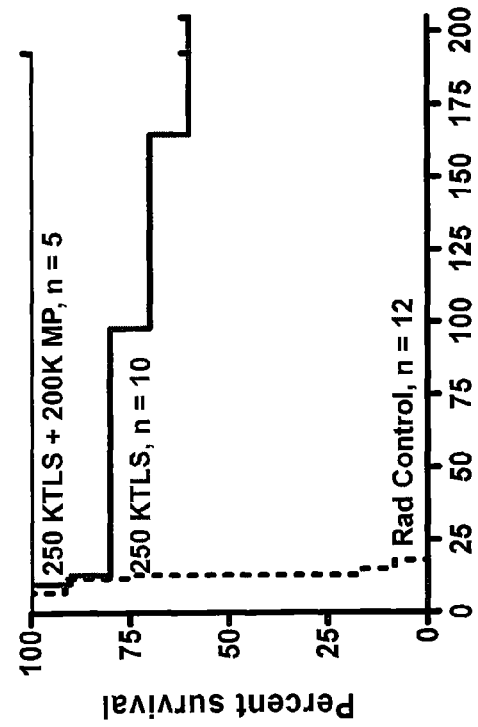
FIG. 4 shows survival data in the allogeneic (matched unrelated donor) transplant model.
Figure 4A:
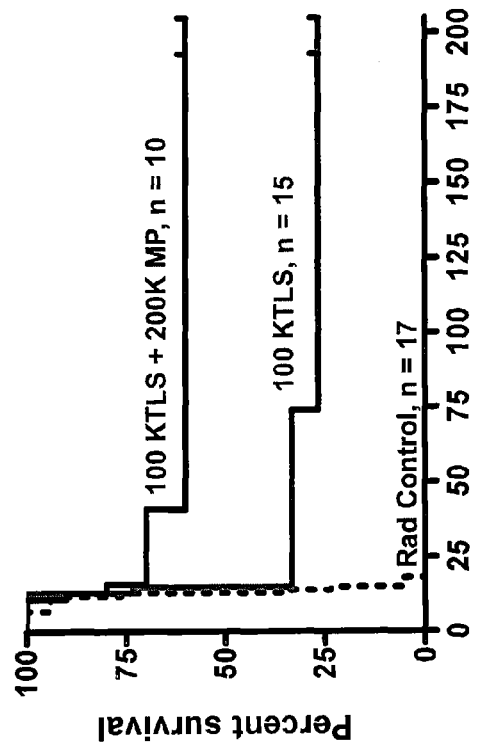

FIG. 4 shows survival data in the allogeneic (matched unrelated donor) transplant model. 100 (FIG. 4A) or 250 (FIG. 4 B) KTLS C57B6/Ka (Thy-1.1, CD45.2, H2b) HSC were transplanted alone or in combination with 200,000 C57B6/Ka (Thy-1.1, CD45.2, H2b) MP into 129 (CD45.1, H2b) hosts. FIG. 4 shows that the addition of MP to the HSC graft improved survival at both, 100 and 250, stem cell doses.

Figure 5A:
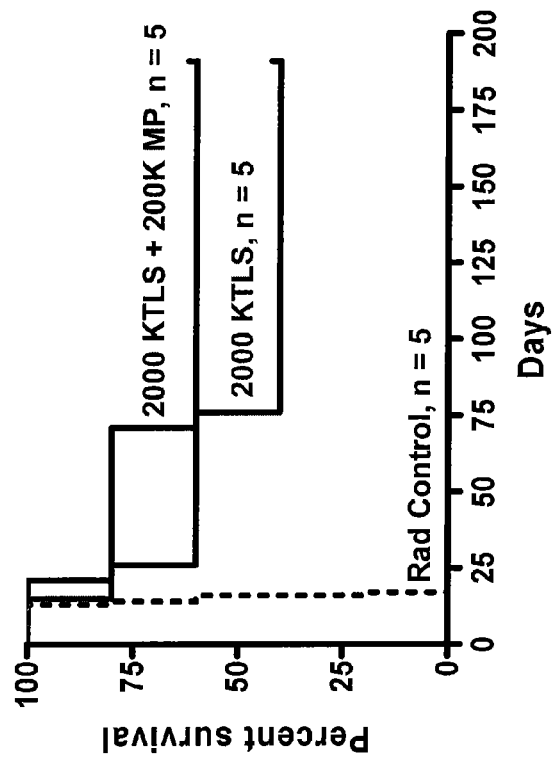
FIG. 5 shows survival data in the allogeneic (completely mismatched) transplant model.
Figure 5B:
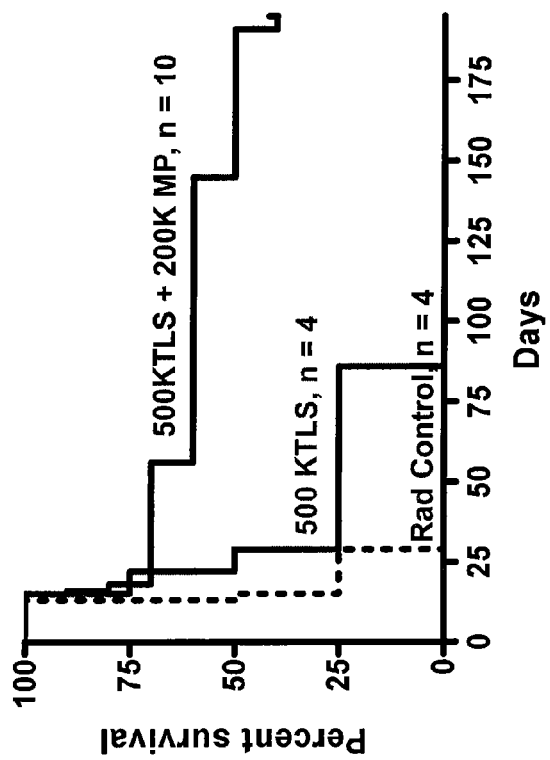

FIG. 5 shows survival data in the allogeneic (completely mismatched) transplant model. 500 (FIG. 5A) or 2000 (FIG. 5B) KTLS C57B6/Ka (Thy-1.1, CD45.2, H2b) HSC were transplanted alone or in combination with 200,000 C57B6/Ka (Thy-1.1, CD45.2, H2b) MP into Balb/c (CD45.1, H2d) hosts. FIG. 5 shows that the addition of MP to the HSC graft improved survival at both, 500 and 2000, stem cell doses.

FIG. 6 summarizes the survival and chimerism data for the three transplant models (syngeneic, matched unrelated donor, and mismatched allogeneic).

In all three models, syngeneic, MUD and mismatched allogeneic, the inclusion of MP in combination with suboptimal doses of HSC improved survival over HSC alone.

7.3 Example 3

Use of Allogeneic Culture-Derived Myeloid Progenitors Cells to Augment Survival in Conjunction with Sub-Optimal Doses of HSC This study was designed to determine if inclusion of allogeneic culture-derived MP could improve survival following matched unrelated donor (MUD) HSC transplantation when HSC dose is below the dose required to provide radioprotection.

HSC were prepared from mouse bone marrow (BM), and $Lin^{neg/low}$ KTLS-HSCs were sorted from AKR mice (H-2k, CD90.1, CD45.2). Sorted cells were plated in serum-free medium supplemented with c-KitL, FL, TPO and IL-6. The cells were cultured for 7 days. Following the culture period cells were harvested, analyzed by FACS for MP (CMP/GMP/MEP) and HSC content and frozen. FIG. 8 shows the analysis of AKR (Thy-1.1, CD45.2, H2k) cultured derived MP.

On the day of the transplant, $Lin^{neg}$ KTLS-HSCs were sorted from C57B1/Ka (H-2b, CD90.1, CD45.1) mice FIG. 7. AKR KTLS HSC were sorted and cultured as described for 7 days. Following this culture period cells were analyzed and frozen. The cell dose for transplantation is calculated based on the number of c-kit$^+$ cells in the culture.

Host-mice, 129 (H-2b, CD90.2, CD45.2), were lethally irradiated using split dose irradiation (11.5Gy total dose, cesium source) at day 0. The cultured cells were thawed and reanalyzed by FACS for viability, and analyzed for MP (CMP/GMP/MEP) and HSC content. Total cell numbers and HSC and MP cell numbers are calculated from the sorting analysis. The cells used for injection into mice are unstained. The culture-derived MP were combined with the desired number of HSC and transplanted into the conditioned hosts by retro-orbital injection.

FIG. 9 shows survival data in transplantation model in which matched unrelated donor KTLS HSC were co-transplanted with completely mismatched allogeneic culture derived MP. 100 KTLS C57B6/Ka (Thy-1.1, CD45.1, H2b) HSC were transplanted alone or in combination with 500,000 c-kit+AKR (Thy-1.1, CD45.2, H2k) cultured derived MP (MPc) into 129 (CD45.2, H2d) hosts. The addition of MPc to the HSC graft improved survival. The survival from the combined graft is greater than transplanting either the same dose of HSC or MPc alone.

In this model, the combined graft of allogeneic (MUD) HSC and third party allogeneic culture-derived MPs enhanced survival over either HSC or MP alone (FIG. 9).

FIG. 10 shows survival data in a transplantation model in which MHC matched unrelated donor HSC were co-transplanted with MPc derived from 2 MHC mismatched donors. 50 allogeneic HSC (Balb/b, H-2b) were transplanted alone or in combination with 1 or 2 million pooled allogeneic culture derived MP (FVB, H-2q; AKR, H2k) into lethally irradiated hosts (C57B1/Ka, H-2b). The addition of MPc to the HSC graft improved survival as compared to HSC alone. The combined graft of HSC and MPc had improved survival as compared to either HSC or MPc transplantation alone.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

All patents, patent applications, publications, and references cited herein are expressly incorporated by reference to the same extent as if each individual publication or patent application was specifically and individually indicated to be incorporated by reference.

What is claimed is:

1. A method of enhancing engraftment of an allogeneic hematopoietic stem cell (HSC) graft in a patient, comprising administering the HSC graft to said patient at a suboptimal dose in conjunction with an expanded allogeneic myeloid progenitor (MP) cell graft comprising common myeloid progenitor (CMP) cells, granulocyte/macrophage progenitor (GMP) cells, and megakaryocyte/erythroid progenitor (MEP) cells in an amount effective to enhance the engraftment of the hematopoietic stem cells, wherein the myeloid progenitor cell graft comprises a population of pooled, culture-expanded, myeloid progenitor cells from multiple unrelated donors, wherein the MP cell graft enhances engraftment of the HSC graft suboptimal dose, thereby enhancing engraftment of the HSC graft.

2. The method of claim 1, wherein the suboptimal HSC graft comprises less than $5.0 \times 10^6$ CD34$^+$ hematopoietic stem cells (HSCs) per kg patient body weight.

3. The method of claim 1, wherein the suboptimal HSC graft comprises less than $1.0 \times 10^6$ CD34$^+$ HSCs per kg patient body weight.

4. The method of claim 1, wherein the suboptimal HSC graft is obtained from peripheral blood or bone marrow.

5. The method of claim 1, wherein the suboptimal HSC graft is obtained from umbilical cord blood (UBC).

6. The method of claim 5, wherein the suboptimal HSC graft comprises less than $4 \times 10^7$ nucleated cells per kg patient body weight.

7. The method of claim 5, wherein the suboptimal HSC graft comprises less than $4.0 \times 10^5$ CD34$^+$ cells per kg patient body weight.

8. The method of claim 5, wherein the suboptimal HSC graft comprises HSCs obtained from less than two cord blood units.

9. The method of claim 5, wherein the suboptimal HSC graft comprises HSCs obtained from a single cord blood unit.

10. The method of claim 1, wherein said allogeneic MP cell graft and said HSC graft are at least partially mismatched at the major histocompatability complex (MHC) with respect to the patient.

11. The method of claim 1, wherein said myeloid progenitor cell graft is administered concurrently with said hematopoietic stem cell graft.

12. The method of claim 1, wherein said myeloid progenitor cell graft is administered within 12 hours of said hematopoietic stem cell graft.

13. The method of claim 1, wherein said allogeneic myeloid progenitor cells are at least partially mismatched at the major histocompatability complex (MHC) with respect to the hematopoietic stem cell graft.

* * * * *